US012780833B2

(12) United States Patent
Mitton-Fry

(10) Patent No.: US 12,780,833 B2
(45) Date of Patent: Nov. 3, 2026

(54) BACTERIAL TOPOISOMERASE INHIBITORS DERIVED FROM ISOMANNIDE

(71) Applicant: Ohio State Innovation Foundation, Columbus, OH (US)

(72) Inventor: Mark Mitton-Fry, Granville, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 913 days.

(21) Appl. No.: 17/794,962

(22) PCT Filed: Jan. 22, 2021

(86) PCT No.: PCT/US2021/014708
§ 371 (c)(1),
(2) Date: Jul. 23, 2022

(87) PCT Pub. No.: WO2021/150954
PCT Pub. Date: Jul. 29, 2021

(65) Prior Publication Data

US 2023/0097866 A1 Mar. 30, 2023

Related U.S. Application Data

(60) Provisional application No. 62/965,507, filed on Jan. 24, 2020.

(51) Int. Cl.
*C07D 493/04* (2006.01)
*A61P 31/04* (2006.01)
*C07D 519/00* (2006.01)

(52) U.S. Cl.
CPC ............ *C07D 493/04* (2013.01); *A61P 31/04* (2018.01); *C07D 519/00* (2013.01)

(58) Field of Classification Search
CPC ............................ C07D 493/04; C07D 519/00
See application file for complete search history.

(56) References Cited

U.S. PATENT DOCUMENTS

2009/0162478 A1 6/2009 Abend et al.
2012/0183660 A1 7/2012 Tachdjian et al.
2013/0295261 A1 11/2013 Tachdjian et al.

FOREIGN PATENT DOCUMENTS

EP 3287462 A1 2/2018

OTHER PUBLICATIONS

Extended European Search Report issued for Application No. 21745081.6, dated Dec. 12, 2023.

Office Action, dated Sep. 28, 2023, received in connection with related EP Patent Application No. 20810128.7.

International Searching Authority (ISA/US). International Search Report and Written Opinion, issued n PCT Application No. PCT/US2021/014708 on Apr. 15, 2021. 8 pages.

Okumu, Antony, et al. "Novel bacterial topoisomerase inhibitors derived from isomannide." European journal of medicinal chemistry 199 (2020): 1-17.

*Primary Examiner* — Matthew P Coughlin
(74) *Attorney, Agent, or Firm* — Meunier Carlin & Curfman LLC

(57) ABSTRACT

Disclosed are bacterial topoisomerase inhibitors employing a linker derived from isomannide. Reduced hERG inhibition was observed compared to structure-matched analogues with different linkers.

32 Claims, No Drawings

BACTERIAL TOPOISOMERASE INHIBITORS DERIVED FROM ISOMANNIDE

CROSS REFERENCE TO RELATED APPLICATIONS

This application is a national stage application filed under 35 U.S.C. § 371 of PCT/US2021/014708, filed Jan. 22, 2021, which claims the benefit of priority to U.S. Provisional Application 62/965,507, filed Jan. 24, 2020, which is incorporated by reference herein in its entirety.

BACKGROUND

In its 2019 report on antibiotic resistance, the United States Centers for Disease Control and Prevention (CDC) classified MRSA as a serious threat and ranked it second only to *Clostridioides difficile* as a source of mortality, with >10,000 deaths per year in the U.S. While the past decade has seen numerous new medicines approved for MRSA infection, morbidity and mortality remain unacceptably high, and new therapeutic options are badly needed.

Novel bacterial topoisomerase inhibitors (NBTIs) (Mitton-Fry, M. J. Novel Bacterial Type II Topoisomerase Inhibitors. *Med. Chem. Rev.* 2017, 52, 281-302) have emerged as a promising strategy for the cure of infections caused by MRSA and other antibiotic-resistant bacteria. Importantly, however, the NBTIs hind to a novel site (Bax, B. D., et al., Type IIA Topoisomerase Inhibition by a New Class of Antibacterial Agents. *Nature* 2010, 466, 935-940) and exhibit mechanistic differences from the fluoroquinolones (Bax, B. D., et al., Type IIA Topoisomerase Inhibition by a New Class of Antibacterial Agents, *Nature* 2010, 466, 935-940; Gibson, E. G., et al., Mechanistic and Structural Basis for the Actions of the Antibacterial Gepotidacin against *Staphylococcus aureus* Gyrase. *ACS Intect. Dis.* 2019, 5, 570-581; Gibson, E. G., et al., Bimodal Actions of a Naphthyridinone/Aminopiperidine-Based Antibacterial that Targets Gyrase and Topoisomerase *Biochem.* 2019, 58, 4447-4455). As a result, the NBTIs lack cross-resistance with fluoroquinolones. Challenges to the success of the NBTI class remain, however, including cardiovascular safety concerns associated with hERG inhibition (Kolarie, A., et al., Novel Bacterial Topoisomerase Inhibitors: Challenges and Perspectives in Reducing hERG Toxicity. *Future Med. Chem.* 2018, 10, 2241-2244).

Disclosed herein is the design and synthesis of Mils with reduced basicity. Reck and coworkers previously revealed the potential of such a tactic, identifying AZD9742 as a clinical candidate through basicity reduction by the electronegative fluoro substituent (Reck, F., et al., Novel N-Linked Aminopiperidine Inhibitors of Bacterial Topoisomerase Type II with Reduced pKa: Antibacterial Agents with an Improved Safety Profile. *J. Med Chem.* 2012, 55, 6916). Another approach entailed the use of a 1,3-dioxane linker in which basicity was reduced by the two neighboring electronegative oxygen atoms (Li, L., et al., Synthesis and Anti-Staphylococcal activity of Novel Bacterial Topoisomerase Inhibitors with a 5-Amino-1,3-Dioxane Linker Moiety. *Bioorg. Med. Chem. Lett.* 2018, 28, 2477-2480). More recently, additional analogues were reported in which the weakly basic secondary amine was replaced with a secondary amide (Li, L., et al., 1,3-Dioxane-Linked Bacterial Topoisomerase inhibitors with Enhanced Antibacterial Activity and Reduced hERG Inhibition. *ACS Infect. Dis.* 2019, 5, 1115-1128). Disclosed herein are results focused on NBTIs with potent anti-MRSA activity, here employing a linker moiety derived from isomannide (e.g., as in comound 6, Scheme 3).

SUMMARY

In accordance with the purposes of the disclosed materials and methods, as embodied and broadly described herein, the disclosed subject matter, in one aspect, relates to compounds, compositions and methods of making and using compounds and compositions. In specific aspects, the disclosed subject matter relates to Novel Bacterial Type II Topoisomerase Inhibitors (NBTIs), analogs thereof, pharmaceutical compositions thereof, and methods of making and using these compounds and compositions. In further aspects, the disclosed subject matter relates to NBTIs with both gyrase and TopoIV activity, analogs thereof, pharmaceutical compositions thereof, and methods of making and using these compounds and compositions. The disclosed compounds can have potent and balanced inhibition of gyrase and TopoIV (to maximize bacterial killing and slow resistance emergence), minimal hERG inhibition (to reduce cardiotoxicity liabilities), and physicochemical properties consistent with desirable pharmacokinetic (PK) properties. Methods of using the disclosed compounds to treat infections, such as MRSA, MDR *P. aeruginosa*, and other pathogens are also described herein.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

The materials, compounds, compositions, and methods described herein may be understood more readily by reference to the following detailed description of specific aspects of the disclosed subject matter, and the Examples included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the specification and claims the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise, Thus, for example, reference to "a composition" includes mixtures of two or more such compositions, reference to "an inhibitor" includes mixtures of two or more such inhibitors, reference to "the kinase" includes mixtures of two or more such kinases, and the like.

"Optional" or "optionally" means that the subsequently described event or circumstance can or cannot occur, and that the description includes instances where the event or circumstance occurs and instances where it does not.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used. Further, ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. Unless stated otherwise, the term "about" means within 5% (e.g., within 2% or 1%) of the particular value modified by the term "about."

By "reduce" or other forms of the word, such as "reducing" or "reduction," is meant lowering of an event or characteristic (e.g., bacterial growth or infection). It is understood that this is typically in relation to some standard or expected value, in other words it is relative, hut that it is not always necessary for the standard or relative value to be referred to. For example, "reduces bacterial growth" means decreasing the amount of bacteria cells relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

As used herein, "treatment" refers to obtaining beneficial or desired clinical results. Beneficial or desired clinical results include, but are not limited to, any one or more of: alleviation of one or more symptoms (such as bacterial growth or infection), diminishment of extent of infection, stabilized not worsening) state of infection, preventing or delaying spread of the infection, preventing or delaying occurrence or recurrence of infection, delay or slowing of infection progression, and amelioration of the infected state.

The term "patient" preferably refers to a human in need of treatment for any purpose, and more preferably a human in need of a treatment to treat infection. However, the term "patient" can also refer to non-human animals, preferably mammals such as dogs, cats, horses, cows, pigs, sheep and non-human primates, among others, that are in need of treatment with a compound as disclosed herein.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "composition" is intended to encompass a product comprising the specified ingredients in the specified amounts, as well as any product which results, directly or indirectly, from combination of the specified ingredients in the specified amounts.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valenci es of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms ($C_1$-$C_{24}$), such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. In specific examples, an alkyl group can be $C_1$-$C_{18}$, $C_1$-$C_{10}$, or $C_1$-$C_6$ alkyl.

The symbols A" is used herein as merely a generic substituent in the definitions below.

The term "alkoxy" as used herein is an alkyl group, as defined herein, bound through a single, terminal ether linkage; that is, an "alkoxy" group can be defined as $OA^1$ where $A^1$ is alkyl as defined above.

The term "alkenyl" as used herein is a hydrocarbon group of from 2 to 24 carbon atoms with a structural formula containing at least one carbon-carbon double bond ($C_2$-$C_{24}$). Asymmetric structures such as $(A^1A^2)C{=}C(A^3A^4)$ are intended to include both the E and Z isomers. This may be presumed in structural formulae herein wherein an asymmetric alkene is present, or it may be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. In specific examples, an alkenyl group can be $C_2$-$C_{18}$, $C_2$-$C_{10}$, or $C_2$-$C_6$ alkenyl.

The term "alkynyl" as used herein is a hydrocarbon group of 2 to 24 carbon atoms with a structural formula containing at least one carbon-carbon triple bond ($C_2$-$C_{24}$). The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below. In specific examples, an alkynyl group can be $C_2$-$C_{18}$, $C_2$-$C_{10}$, or $C_2$-$C_6$ alkynyl.

The term "aryl" as used herein is a group that contains any carbon-based aromatic group having from 5 to 15 carbon atoms including, but not limited to, benzene, naphthalene, phenyl, biphenyl, pherioxybenzene, and the like. The term "heteroaryl" is defined as a group that contains an aromatic group that has from 4 to 15 carbon atoms and at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl and heteroaryl group can be substituted or unsubstituted. The aryl and heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of from 3 to 15 carbon atoms. Examples of cycloalkyl groups include, but are not limited to, cyclopropyl, cyclobutyl, cyclopentyl cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfa-oxo, sulfonyl, sulfone, sulfoxide, or thiol as described herein.

The term "cycloalkenyl" as used herein is a non-aromatic carbon-based ring composed of from 3 to 15 carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" is a short hand notation for C=O, which is also referred to as oxo.

The terms "amine" or "amino" as used herein are represented by the formula $NA^1A^2A^3$, where $A^1$, $A^2$, and $A^3$ can be, independently, hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylase" as used herein is represented by the formula $—C(O)O^-$.

The term "ester" as used herein is represented by the formula $—OC(O)A^1$ or $—C(O)OA^1$, where $A^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $A^1OA^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $A^1C(O)A^2$, where $A^1$ and $A^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" as used herein refers to the halogens fluorine, chlorine, bromine, and iodine.

The term "hydroxyl" as used herein is represented by the formula —OH.

The term "nitro" as used herein is represented by the formula —$NO_2$.

The term "cyano" as used herein is represented by the formula —CN

The term "azido" as used herein is repressed by the formula —$N_3$.

The term "sulfonyl" is used herein to refer to the sulfo-oxo group represented by the formula —$S(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above. The terms "suifoxide" is used herein to refer to the sulfo-oxo group represented by the formula —$OS(O)_2A^1$, where $A^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH_2$.

The term "thiol" as used herein is represented by the formula —SH.

As used herein, the symbol

(hereinafter can be referred to as "a point of attachment bond") denotes a bond that is a point of attachment between two chemical entities, one of which is depicted as being attached to the point of attachment bond and the other of which is not depicted as being attached to the point of attachment bond. For example,

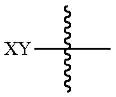

indicates that the chemical entity "XV" is bonded to another chemical entity via the point of attachment bond. Furthermore, the specific point of attachment to the non-depicted chemical entity can be specified by inference. For example, the compound $CH_3$—$R^3$, wherein $R^3$ is H or

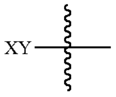

infers that when $R^3$ is "XY", the point of attachment bond is the same bond as the bond by which $R^3$ is depicted as being bonded to $CH_3$.

It is to be understood that the compounds provided herein may contain chiral centers. Such chiral centers may be of either the (R-) or (S-) configuration. The compounds provided herein may either be enantiomerically pure, or be diastereomeric or enantiomeric mixtures. It is to be understood that the chiral centers of the compounds provided herein may undergo epimerization in vivo. As such, one of skill in the art will recognize that administration of a compound in its (R-) form is equivalent, for compounds that undergo epimerization in vivo, to administration of the compound in its (S-) form.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A "pharmaceutically acceptable" component is one that is suitable for use with humans and/or animals without undue adverse side effects (such as toxicity, irritation, and allergic response) commensurate with a reasonable benefit/risk ratio.

"Pharmaceutically acceptable salt" refers to a salt that is pharmaceutically acceptable and has the desired pharmacological properties. Such salts include those that may be formed where acidic protons present in the compounds are capable of reacting with inorganic or organic bases. Suitable inorganic salts include those formed with the alkali metals, e.g., sodium, potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). When two acidic groups are present, a pharmaceutically acceptable salt may be a mono-acid-mono-salt or a di-salt; similarly, where there are more than two acidic groups present, some or all of such groups can be converted into salts.

"Pharmaceutically acceptable excipient" refers to an excipient that is conventionally useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

A "pharmaceutically acceptable carrier" is a carrier, such as a solvent, suspending agent or vehicle, for delivering the disclosed compounds to the patient. The carrier can be liquid or solid and is selected with the planned manner of administration in mind. Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. In reference to infection, an effective amount comprises an amount sufficient to cause a bacterial cell to shrink and/or to decrease the growth rate of the bacterial cells or to prevent or delay other unwanted infection. In some embodiments, an effective amount is an amount sufficient to delay development. In some embodiments, an effective amount is an amount sufficient to prevent or delay occurrence and/or recurrence. An effective amount can be administered in one or more doses. In the case of bacterial infection, the effective amount of the drug or composition may: (i) reduce the number of bacterial cells; (ii) reduce bacterial cell size; (iii) inhibit, retard, slow to some extent and preferably stop bacterial cell infiltration into peripheral organs; (iv) inhibit bacterial growth; (vi) prevent or delay occurrence and/or recurrence of bacterial infection; and/or (vii) relieve to some extent one or more of the symptoms associated with the infection.

Effective amounts of a compound or composition described herein for treating a mammalian subject can include about 0.1 to about 1000 mg/Kg of body weight of the subject/day, such as from about 1 to about 100 mg/Kg/day, especially from about 10 to about 100 mg/Kg/day. The doses can be acute or chronic. A broad range of disclosed composition dosages are believed to be both safe and effective.

Reference will now be made in detail to specific aspects of the disclosed materials, compounds, compositions, articles, and methods, examples of which are illustrated in the accompanying Examples.

Compounds

Examples of some NBTIs in the literature are provided in Scheme 1. As illustrated by GSK299423 (1) (Bax, B. et al. *Nature* 2010, 466, 935) and summarized by Singh (Singh, S. B., et al. *ACS Med. Chem. Lett.* 2014, 5, 609), NBTIs share three common structural domains: a) a left-hand side (LHS) usually comprising a fused bicyclic or tricyclic ring system, b) a linker domain with an amine positioned to interact with D83 of gyrase, and c) a right-hand side (RHS) comprising an aromatic or heteroaromatic ring. X-ray crystallography has been used to study the binding of these compounds to a complex of gyrase and DNA. This research has provided insight at the molecular level into compound binding (Widdowson, K., et al. *Future Med Chem.* 2010, 2, 1619; Lahiri, S. D., et al. *Antimicrob. Agents Chemother.* 2015, 59, 5278), and this understanding has been enhanced through the study of target mutations conferring resistance to NBTIs.

Scheme 1

(1)

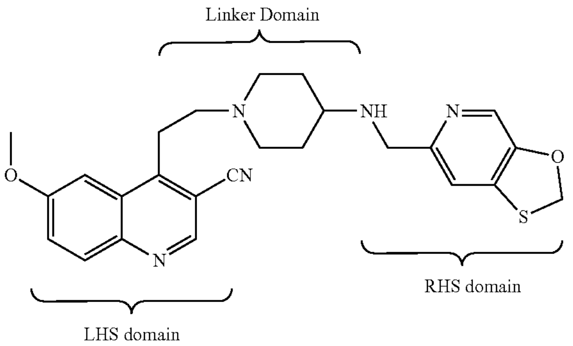

GSK299423

(2)

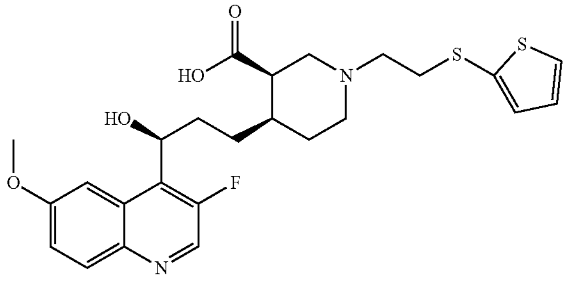

NXL-101

(3)

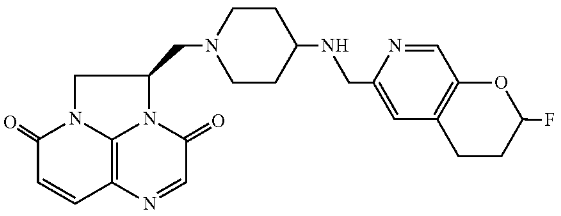

gepotidancin (4)

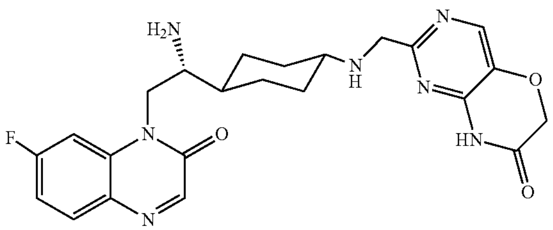

NBTI 5462

(5)

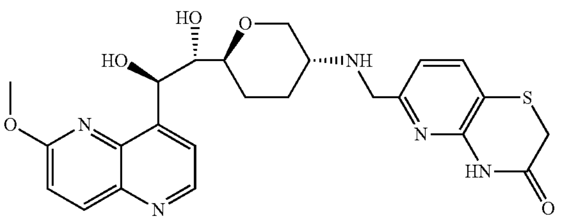

Actellon

-continued (6)

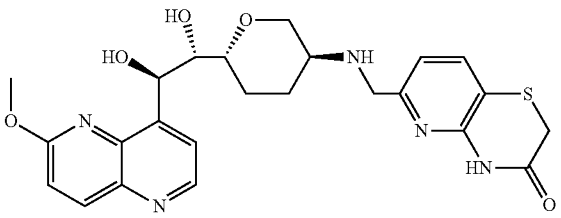

Actellon (7)

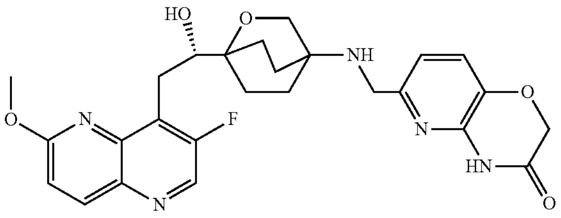

Merk AM8191

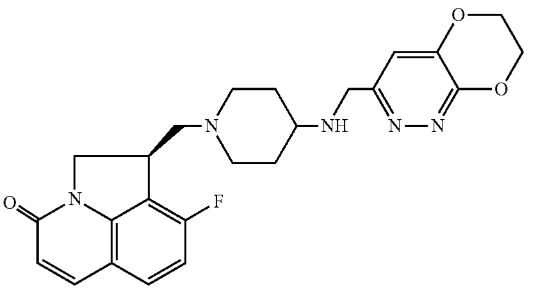

GSK945237

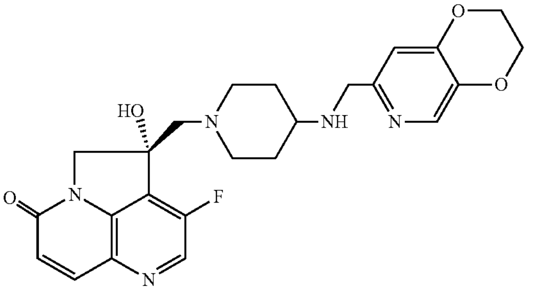

GSK9486587

The LHS binds with uncleaved DNA, and the RHS, generally containing an aromatic or heteroaromatic ring, binds to a dimeric interface of gyrase. Commonly observed gyrase mutations conferring resistance to NBTIs, such as substitutions at D83 and M121, occur at this interface. Extensive previous efforts have optimized the LHS and RES moieties and illustrated the tolerance for structural variety and innovation in the linker (Surivet, J-P., et al, J. Med. Chern. 2017, 60, 3776; Li, L., et al. Bioorg. Med, Chem, Lett. 2018, 28, 2477; Li, L., et al., ACS Infect, Dis. 2019, 5, 1115; Tan. C. M., et al. *Antimicrob. Agents Chemother,* 2016, 60, 4830; Black, M. T., et al. *Antimicrob. Agents Chemother.* 2008, 52, 3339; Mitton-Fry, M. J., et al. *Bioorg Med. Chem. Lett.* 2013, 23, 2955; Dougherty, T. J., et al. *Antimicrob. Agents Chemother.* 2014, 58, 2657; Dougherty, T. J., et al. *Antimicrob. Agents Chemother.* 2014, 58, 4250; Nayar, A. S., et al. *Antimicrob. Agents Chemother.* 2015, 59, 331; Reck, F., et al. *Bioorg. Med Chem.* 2014, 22, 5392; Surivet, J-P., et al. *J. Med Chem.* 2013, 56, 7396; Surivet, J-P., et al. *J. Med Chem.* 2015, 58, 927; Miles, T. J., et al. *Bioorg. Med. Chem. Lett.* 2011, 21, 7489; Wiles, J. A., et al. *J. Med Chem.* 2011, 54, 3418; Mitton-Fry, M. J. Novel, Nonquinolone Inhibitors of DNA Gyrase and Topoisomerase IV: Antibacterial Activity and Resistance Mechanisms, Presented at the 243rd National Meeting of the American Chemical Society, San Diego, CA, 2012, Paper MEDI-257; Singh, S. B., et al. *Bioorg. Med. Chem. Lett.* 2015, 25, 2409; Singh, S. B., et al. *Bioorg. Med. Chem. Lett.* 2015, 25, 3636; Singh, S. B., et al. *Med. Chem. Commun.* 2015, 6, 1773; So, W., et al. *Antimicrob. Agents Chemother.* 2015, 59, 4956; Miles, T. J., et al. *Bioorg Med. Chem. Lett.* 2013, 23, 5437).

The largely solvent-exposed linker domain serves to bridge the LHS and RHS and does not itself play a critical role in binding, evidenced by the linker diversity tolerated in compounds in Scheme 1. In the compounds disclosed herein, a new linker moiety is introduced, which has been found to modulate the physicochemical properties. The structural simplicity and synthetic accessibility of the linker moiety disclosed herein can also result in improved synthetic efficiency and cost effectiveness. Specifically, the disclosed compounds have a 6-amino-hexahydrofuro[3,2-b] furan-3-ol linker moiety, shown below.

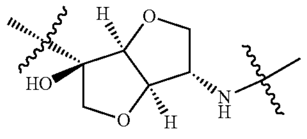 [SMILES: *N[C@H]1CO[C@H]2[C@@H]1OC[C@@]2(*)O]

In the disclosed compounds, this linker moiety can reduce lipophilicity and amine basicity, improving pharmacokinetic and cardiac safety properties (Reck, F., et al.; Novel N-Linked Aminopiperidine Inhibitors of Bacterial Topoisomerase Type II with Reduced $pK_a$: Antibacterial Agents with an Improved Safety Profile. *J. Med. Chem.* 2012, 55, 6916-6933).

In some aspects, disclosed herein are compounds that are Type II Topoisomerase Inhibitors having Formula I.

I

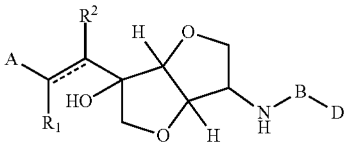

wherein

- the dashed line represents a bond that is present or absent, and when the bond is present, $R^1$ and $R^2$ can be cis or trans;
- A is a fused bicyclic aryl or bicyclic heteroaryl ring optionally substituted with $C_1$-$C_{24}$ alkyl, $C_1$-$C_{24}$ haloalkyl, alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, amide, carboxylic acid, carboxylic ester, ether, carbamate, halide, hydroxy, ketone, cyano, nitro, silyl, sulfo-oxo, sulfonyl, sulfone, sulfoxide, or thiol; or A and $R^1$ together form a tricyclic ring optionally substituted with $C_1$-$C_{24}$ alkyl, $C_1$-$C_{24}$ haloalkyl, $C_1$-$C_{24}$ alkoxy, $C_2$-$C_{24}$ alkenyl, $C_2$-$C_{24}$ alkynyl, $C_4$-$C_{15}$ aryl, $C_4$-$C_{15}$ heteroaryl, aldehyde, amino, arnido, carboxylic acid, carboxylic ester, ether, halide, hydroxy, ketone, cyano, nitro, silyl, sulfo-oxo, sulfonyl, sulfone, sulfoxide, or thiol;

B is $C_1$-$C_6$ alkyl or $C_4$-$C_6$ cycloalkyl optionally substituted with one or more oxo, $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

D is an $C_5$-$C_{15}$ aryl or $C_5$-$C_{15}$ heteroaryl ring optionally substituted with $C_1$-$C_{24}$ alkyl, $C_1$-$C_{24}$ haloalkyl, $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, amino, carboxylic acid, carboxylic ester, carbamate, ether, halide, hydroxy, ketone, nitro, silyl, sulfo-oxo, sulfonyl, sulfone, sulfoxide, or thiol;

$R^1$ and $R^2$ are, independently, chosen from H, OH, Cl, F, Br, CN, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, oxo (i.e =O), and $C_1$-$C_6$ alkyl or $C_1$-$C_6$ alkoxyl optionally substituted with $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol; or $R^1$ is a $C_1$-$C_3$ alkyl or $C_2$-$C_3$ alkenyl, optionally substituted with $R^9$, also bound to A;

each $R^3$ is, independently, chosen from $C_1$-$C_6$ alkyl, $C_1$-$C_6$ cycloalkyl, $C_5$-$C_{15}$ aryl, $C_4$-$C_{15}$ heteroaryl, $C_3$-$C_{15}$ heterocycloalkyl, and $C_1$-$C_{15}$ heteroalkyl, any of which are optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, cyano, ketone, nitro, silyl, sulfo-oxo, sulfonyl, sulfone, sulfoxide, or thiol; and $R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NJ_2$, C(O) $NHR^3$, or $C_1$-$C_6$ alkyl or $C_1$-$C_6$ alkoxyl optionally substituted with $C_1$-$C_{24}$ alkoxy, $C_2$-$C_{24}$ alkenyl, $C_2$-$C_{24}$ alkynyl, $C_5$—$Cr_5$ aryl, $C_4$—$Cr_5$ heteroaryl, aldehyde, amino, carboxylic acid, ester, ether, halide, hydroxy, ketone, cyano, nitro, silyl, sulfa-oxo, sulfonyl, sulfone, sulfoxide, or thiol;

or a pharmaceutically acceptable salt thereof.

Formula I contemplates each enantiomer and diastereomer. A specific example, the stereochemistry of Formula I is:

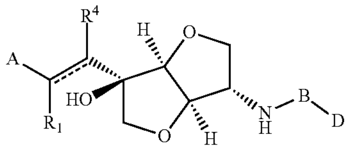

In specific examples of Formula I, the dashed line represents a bond and Formula I can thus be represented as Formula IA ($R^1$ and $R^2$ are trans) or IB ($R^1$ and $R^2$ are cis),

IA

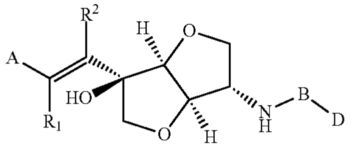

-continued

IB

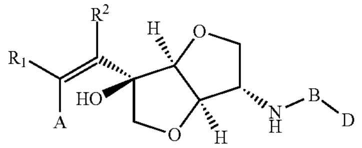

In still other examples, the dashed line in Formula I is absent and Formula I can thus be represented as Formula IC.

IC

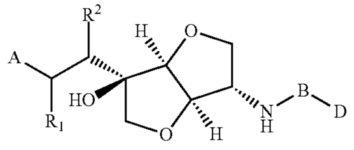

In each of these formulas, the variables $R^1$, $R^2$, $R^3$, $R^9$, A, B, D are as defined herein. Further, unless specifically stated, reference to Formula I herein includes individual references to each of Formulas IA-IC.

The disclosed compounds can have potent and balanced inhibition of gyrase and TopoIV (to maximize bacterial killing and slow resistance emergence), rririmal hERG inhibition (to reduce cardiotoxicity liabilities), and physicochemical properties consistent with desirable pharmacokinetic (PK) properties (Lipinski, C. A., et al. *Adv. Drug Delivery Rev.* 1997, 23, 3; Veber, D. F., et al. *J. Med Chem.* 2002, 45, 2615; Gleeson, M. P. *J Med. Chem.* 2008, 51, 817; Leeson, P. D., et al. *Nature Rev. Drug Disc.* 2007, 6, 881), and ease of synthesis. Further, these compounds can utilize a mechanistically distinct form of topoisomerase inhibition resulting in antibacterial activity even against highly FQ-resistant strains.

Previous work with NBTIs has helped to clarify their advantages and remaining challenges. The interactions with the target, distinct from those of IFQs, lead to a lack of cross-resistance between these two classes of topoisomerase inhibitors (Black, M. T., et al. *Antimicrob. Agents Chemother,* 2008, 52, 3339; Mitton-Fry, M. J.; Brickner, S. J., et al, *Bioorg. Med. Chem. Lett.* 2013, 23, 2955). As such, NBTIs do not face the issue of widespread preexisting resistance in the clinic that would be encountered with a novel FQ, Excellent efficacy against Grain-positive pathogens such as MRSA, both in vitro (Minimum Inhibitory Concentrations, MICs) and in vivo (murine models of infection) has been demonstrated for structurally diverse NBTIs. More recent work has also suggested that an appropriately situated primary amine in the linker domain, such as that found in NBTI5463 (4, Scheme 1) may be sufficient for antibacterial activity against critically important Gram-negative pathogens such as *P. aeruginosa* (Dougherty, T. J., et al. *Antimicrob. Agents Chemother,* 2014, 58, 2657; Dougherty, T. J., et al. *Antimicrob. Agents Chemother.* 2014, 58, 4250; Nayar, A. S., et al. *Antimicrob. Agents Chemother.* 2015, 59, 331; see also Surivet, J-P., et al. *J. Med. Chem.* 2017, 60, 3776) potentially as a result of improved porin penetration. Such effects have also been observed with amine incorporation in other antibacterial drug classes such as cephalosporins.

Among the challenges associated with NBTIs, two deserve special attention. hERG inhibition, with attendant concern about QT-prolongation and cardiovascular safety, must be closely monitored (Li, L., et al. *ACS Infect. Dis.* 2019, 5, 1115; Kolarič, A., et al., *Future Med. Chem.* 2018, 10, 2241-2244; Li, L., et al. *Bioorg. Med Chem. Lett.* 2018, 28, 2477; Surivet, J-P., et al. *J. Med. Chem.* 2017, 60, 3776; Reck, F., et al. *Bioorg. Med. Chem.* 2014, 22, 5392; Miles, T, J., et al. *Bioorg. Med. Chem. Lett.* 2011, 21, 7483; Geng, B., et al. *Bioorg. Med Clicin. Lett.* 2011, 21, 5432; Reck, F., et al. *J. Med. Chem.* 2011, 54, 7834; Reck, F., et al. *J. Med Chem.* 2012, 55, 6916; Wiles, J. A., et al. *J. Med. Chem.* 2011, 54, 3418; Singh, S. B., et al. *Bioorg. Med. Chem. Lett.* 2015, 25, 1831; Singh, S. B., et al, *Bioorg. Med. Chem, Lett* 2015, 25, 2473). At least one clinical candidate. NXL-101 (2, Scheme 1) (Black, M. T., et al. *Antimicrob. Agents Chemother.* 2008, 52, 3339) was withdrawn from clinical studies as a result of QT-prolongation. Historically, NBTIs demonstrate superior inhibition of gyrase as compared to TopoIV, at least in *S. aureus*, permitting resistance by means of single-step mutations to the gyrase target. Improved inhibition of TopoIV has been associated with diminished resistance (Surivet, J-P., et al. *J. Med Chem.* 2013, 56, 7396; Surivet, J-P., et al. *J. Med. Chem.* 2015, 58, 927).

It has been demonstrated that hERG inhibition from NBTIs often correlates strongly with lipophilicity and amine basicity. While not wishing to be bound by theory, the disclosed 6-amino-hexahydrofuro[3,2-b]furan-3-ol linker moiety can minimize hERG inhibition via reduced amine basicity and lipophilicity and provide ready synthetic accessibility across a wide range of derivatives.

Aside from reducing amine basicity and lipophilicity, the readily accessible 6-amino-hexahydrofuro[3,2-b]furan-3-ol linker also enhances synthetic efficiency compared to tetrahydropyran (HIP) and oxabicyclooctane linkers (Scheme 1). THPs 5, 6, and oxabicylooctane 7 all display excellent antibacterial activity, reinforcing the tolerance for structural changes to the linker, provided that the overall molecular topology is maintained. However, synthesis of the linker alone for 7 required 14 steps, and 5 and 6 suffer from synthetic and stereochemical complexity.

In addition to structural diversity, the disclosed compounds can be used to explore a breadth of physicochemical properties, including CLogP and topological polar surface area (TPSA). Variations in LHS, linker substitution, and RHS can be explored systematically. The LHS plays a key role in interacting with DNA. Quinoline LHS A. (Scheme 2) has been used successfully by several teams (Wiles, J. A., et al., *J. Med. Chem.* 2011, 54, 3418; Mitton-Fry, M. J. Novel, Non-quinolone Inhibitors of DNA Gyrase and Topoisomerase IV: Antibacterial Activity and Resistance Mechanisms. Presented at the 243rd National Meeting of the American Chemical Society, San Diego, CA, 2012, Paper MEDI-257), and 1,5-naphthyridine B (Scheme 2) has likewise seen extensive usage (Li, L., et al., *ACS Infect. Dis.* 2019, 5, 1115; Singh, S. B., et al. *Bioorg. Med. Chem. Lett.* 2015, 25, 2409; Singh, S. B., et al. *Bioorg Med. Chem Lett.* 2015, 25, 3636; Singh, S. et al. *Med. Chem. Commun.* 2015, 6, 1773). LHS C (Scheme 2) dramatically reduces the lipophilicity of the planned analogs (ca. 2 CLogP units versus A) and has been shown to provide potent analogs in several reports. Substitution of the methoxy group of LAS C with fluorine, as in LHS D (Scheme 2), has been shown previously to reduce the undesired inhibition of cardiac ion channels, and D is the core for the promising Gram-negative lead NBTI 5463. Similar evidence for potency has been sought in choosing RHS moieties. The RHS binds to the dimeric gyrase interface and has also been observed to impact target potency against TopoIV. Consequently, variations of the RES are can be used to improved TopoIV potency and diminished resistance. Moreover, the choice of RHS also appears to impact the degree of inhibition of the hERG and other ion channels. Whereas all of these moieties have been used in potent inhibitors, RHS 2-4, especially RHS 4, have shown reduced hERG inhibition as compared to RHS 5 and RHS 6. Notably, RHS 1 is a key feature of Phase 3 clinical candidate gepotidacin, RHS 2 was used for an earlier candidate GSK966587, and RHS 7 constitutes the REIS of the analog used in breakthrough crystallographic studies. The choice of RHS also enables variation in lipophilicity, hydrogen bond donor/acceptor number, and TPSA.

Scheme 2

LHS Moieties

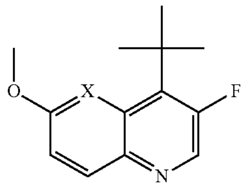

X = CH: LHS A
X = N: LHS B

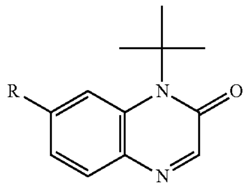

X = OMe: LHS C
X = F: LHS D

General Design Architecture

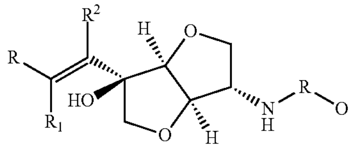

Linker Substitution
$R_1 = R_2 = H$ (LHS A-D)
$R_1 = OH, R_2 = H$ (LHS A, B)
$R_1 = H, R_2 = OH$ (LHS A-D)

RHS Moieties

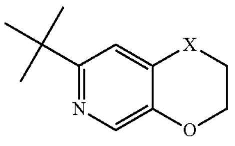

X = CH: RHS 1
X = O: RHS 2

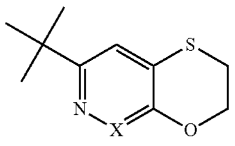

X = CH: RHS 3
X = N: RHS 4

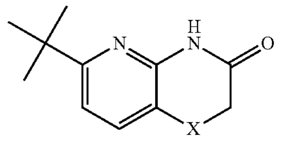

X = O: RHS 5
X = S: RHS 6

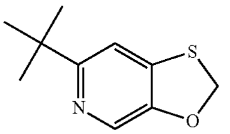

RHS 7

In view of the above, specific examples disclosed herein are compounds of Formula I, wherein A is a fused bicyclic aryl or bicyclic heteroaryl ring having Formula II.

II

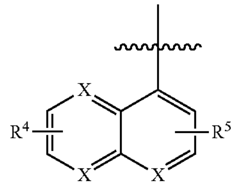

wherein each X is, independently, CH or N; and $R^4$ and $R^5$ are, independently, chosen from H, Cl, F, Br, I, CN, OR, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_5$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can have Formula II, wherein $R^4$ and $R^5$ are, independently, chosen from H, Cl, F, Br, I, CN, OR, and unsubstituted $C_1$-$C_6$ alkyl or $C_1$-$C_6$ alkoxyl further examples, $R^4$ and $R^5$ are, independently, chosen from H, Cl, F, CN, OH, and methoxyl. In further examples, $R^4$ and $R^5$ are, independently, chosen from F and methoxyl. In still further examples, all X's are CH. In yet further examples, one X is CH and the other two X's are N. In yet further examples, two X's are CH and the other X is N. In still further examples, all X's are N.

In further examples, disclosed herein are compounds of Formula I, herein A is a fused bicyclic aryl or bicyclic heteroaryl ring having Formula III.

III

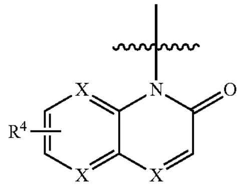

wherein each X is, independently, CH or N;

$R^4$ is chosen from H, Cl, F, Br, I, CN, OR, $NO_2$, $NH_2$, $CF_3$, $CO_2H$, $CO_2NHR^3$, $CO_2R^3$, $C(O)R^3$, $C(O)NH_2$, C(O) $NHR^3$, and $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can have Formula III, wherein $R^4$ is chosen from H, Cl, F, Br, I, CN, OH, and unsubstituted $C_1$-$C_6$ alkyl or $C_1$-$C_6$ alkoxyl. In further examples, $R^4$ is chosen from H, Cl, F, CN, OH, and methoxyl. In further examples, $R^4$ is chosen from F and methoxyl. In specific examples of Formula III, each X is N. In other examples, two X's are CH and the other X is N. In other examples, two X's are N and the other X is CH.

In still further examples, disclosed herein are compounds of Formula I, wherein A is a bicyclic aryl or bicyclic heteroaryl that together with $R^1$ forms a tricyclic ring. When $R^1$ is a $CH_2$, this can be shown by Formula IX, X, XI, or XII.

In specific examples, A can be Formula IX:

IX

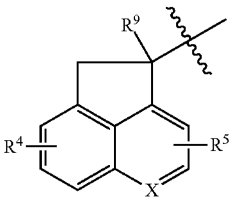

wherein

X is CH, N, or $CR^8$;

$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino; carboxylic acid, ester, ether, halide, hydroxy, ketone, cyano, nitro, silyl, sulfo-oxo, sulfonyl, sulfone, sulfoxide, or thiol; and $R^8$ is Cl, F, CN, OH, $OCH_3$, $CH_3$, or $NH_2$; and $R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfa-oxo, sulfonyl, sulfone, sulfoxide, or thiol.

In specific examples, A can be Formula X:

X

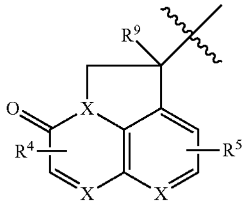

wherein each X is, independently, CH, N, or $CR^8$;

$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfa oxo, sulfonyl, sulfone, sulfoxide, or thiol;

$R^8$ is, independently, Cl, F, CN, OH, $OCH_3$, $CH_3$, or $NH_2$; and $R^9$ is H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, or $C_1$-$C_6$ alkyl or $C_1$-$C_6$ alkoxyl optionally substituted with $C_1$-$C_6$ alkyl, $C_1$-$C_{16}$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, A can be Formula XI:

XI

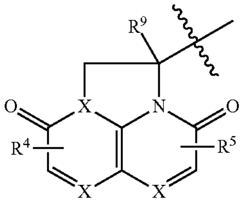

wherein each X is, independently, CH, N, or $CR^8$;

$R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ al kynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

each $R^8$ is, independently, Cl, F, CN, OH, $OCH_3$, $CH_3$, or $NH_2$; and $R^9$ is H or $C_1$-$C_6$ alkyl.

In specific examples, A can be Formula XII:

XII

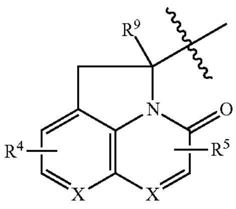

wherein each X is, independently, CH, $N_2$ or $CR^8$, $R^4$ and $R^5$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_6$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

each $R^8$ is, independently, Cl, F, CN, OH, $OCH_3$, $CH_3$, or $NH_2$; and $R^9$ is H or $C_1$-$C_6$ alkyl, In specific examples, of Formula, I, A can be

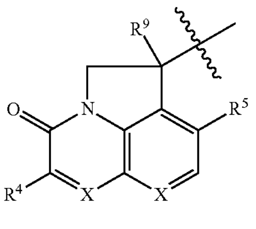

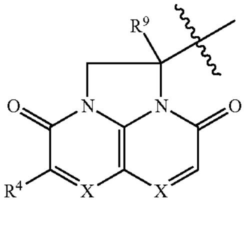

-continued

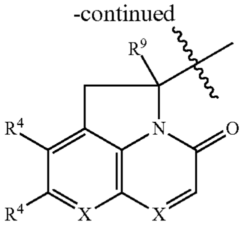

wherein each of $R^4$, $R^5$, $R^8$, and $R^9$ can be independently chosen from Cl, F, CN, OH, $OCH_3$, $CH_3$, or $NH_2$. In preferred examples $R^9$ is H or $CH_3$.

In specific examples, of Formula IX, X, XI, and XII, $R^5$ can be F.

In further examples, disclosed herein are compounds of Formula I, wherein B is a $C_1$-$C_6$ alkyl or $C_4$-$C_6$ cycloalkyl chosen from unsubstituted methyl, ethyl, propyl, butyl, cyclobutyl, or cyclopentyl. In specific examples, B is $CH_2$, —C(=O)—, or cyclobutyl. B can also be CONH or $CH_2NH$—.

In still further examples, disclosed herein are compounds of Formula I, wherein D is aryl or heteroaryl ring having Formula IV-VIII or XIII.

IV

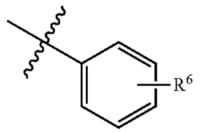

V

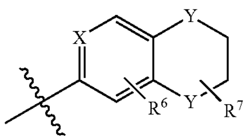

VI

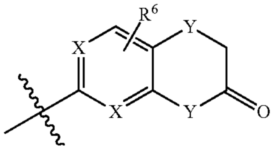

VII

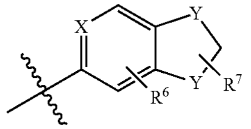

VIII

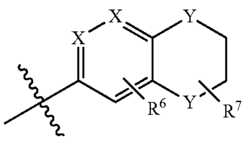

XIII

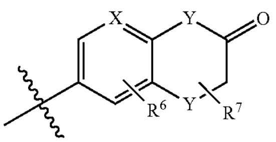

wherein each X is, independently, chosen from CH or N;

each Y is, independently, chosen from O, S, NH, or $CH_2$; and $R^6$ and $R^7$ are, independently, chosen from H, Cl, F, Br, I, CN, OH, $NO_2$, $NH_2$, $CF_3$, $CO_2H$, $CO_2NH_2$, $CO_2NHR^3$, $CO_2R^3$, $C(O)R^3$, $C(O)NH_2$, $C(O)NHR^3$, and $C_1$-$C_6$ alkyl or $C_1$-$C_6$ alkoxyl optionally substituted with $C_1$-$C_6$ alkyl, $C_1$-$C_5$ alkoxyl, $C_2$-$C_6$ alkenyl, $C_2$-$C_6$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol.

In specific examples, D can have Formula or XIII, wherein $R^6$ and $R^7$ are, independently, chosen from H, Cl, F, Br, I, CN, OH, and unsubstituted $C_1$-$C_6$ alkyl or $C_1$-$C_6$ alkoxyl. In further examples, $R^6$ and $R^7$ are, independently, chosen from H, Cl, F, CN, OH, and methoxyl. In further examples, $R^6$ and $R^7$ are, independently, chosen from F and methoxyl. In further examples, $R^6$ and $R^7$ are both H. In still further examples, both Y are O. In other examples, one Y is S and the other is O. In still other examples, one Y is NH and the other is O.

In yet further examples, disclosed herein are compounds of Formula I, wherein $R^1$ and $R^2$ are, independently, chosen from H, F, OH, and $NH_2$. In specific examples, is $NH_2$. In other examples, $R^2$ is H or OH. In further examples, $R^1$ is H or OH. In specific examples, $R^2$ is oxo (i.e., In other examples, $R^1$ is oxo (i.e., =O). Incorporation of a hydroxyl substituent (at $R^1$ or $R^2$) reduces lipophilicity by ca. 1.5 CLogP units and has been shown in some cases to impact hERG inhibition and other properties.

Method of Use

The compounds disclosed herein can be used to treat infections and inhibit the growth of bacteria. In certain examples, disclosed are methods of treating an infection in a patient, comprising administering to the patient a thereapeutically effective amount of any of the compounds disclosed herein. Specific examples of infections that can be treated include, but are not limited to, *Actinobacter, Actinotnycetes, Bacilli, Bortedellen, Clostridia, Corynebacteria, Enterobacter, Enterococci, Helicobacter, Haetnophilus, Listeria, Mycobacteria, Neisseria, Shigella, Salmonella, Streptococci, Staphylococci*, tuberculosis bacteria, and *Yersinia.*

In some examples, the disclosed compounds can be used to treat infections caused by resistant G-pos. bacteria such as Methicillin Resistant *Staphylococcus aureus* (MRSA). Despite newly launched drugs and others in clinical development, the CDC characterizes MRSA as a serious threat, its second highest level of concern. These disclosed methods can involve administering a compound disclosed herein to the infected human or animal or the human or animal at risk of being infected. In some specific examples, the infected individual has cyctic fibrosis.

In some examples, the disclosed compounds can be used to treat infections caused by resistant G-neg. pathogens such as *P. aeruginosa*. Infections caused by G-neg. bacteria in general, and MDR *P. aeruginosa* in particular (Wagner, S., et al. *J. Med. Chem.* 2016, 59, 5929), represent a key need in antibacterial drug discovery that is currently underrepresented by approaches in clinical development. The additional permeability barrier imposed by the outer membrane of G-neg. organisms (Zgurskaya, H. I., et al. *ACS Infect. Dis.* 2015, 1, 512), as well as other resistance mechanisms such as robust multidrug efflux transporters, make the identification of potential new therapies particularly challenging. These disclosed methods can involve administering a compound disclosed herein to the infected human or animal or the human or animal at risk of being infected.

In still other examples, the disclosed compounds can be used to treat infections by *M. tuberculosis, M. avium*, or *M. abscesses.*

In some examples, the disclosed compounds can be used to treat infections caused by *Enterococcus faecturn, Klebsiella pneumoniae, Acinetobacter baumannii*, various *Enterobacter*, and *Neisseria gonorrhoeae*. Further examples include the following diseases include: tuberculosis; Pneumonia; Typhoid; Paratyphoid; Syphilis, Gastritis; Gastroenteritis; Ruhr; Pestilence; Enteritis; extraintestinal infections, peritonitis and appendicitis with *E. coli* and intestinal infections with EHEC, EPEC, ETEC and EIEC; Cholera, Legionnaires' disease, whooping cough, brucellosis, Lyme disease, leptospirosis, typhus, trachoma, gonorrhea, meningitis, septicemia, leprosy etc. These methods can involve administering a compound disclosed herein to the infected human or animal or the human or animal at risk of being infected.

In other examples, disclosed herein are methods of treating an infection in a patient, comprising administering to the patient a thereapeutically effective amount of any of the compounds disclosed herein.

In these disclosed methods, one can treat humans with infections, but also can treat livestock (horses, cows, pigs, sheep, goats etc.), poultry, and companion animals (dogs, cats, rabbits, etc.). The compositions or organisms can be administered alone or in combination with other therapeutics or nutritional supplements, for example the composition can be combined into a feed.

Combinations

The disclosed compounds can also be combined with additional antimicrobial agents. For example, the disclosed compounds can be combined with one or more of Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Aziocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bipyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphaniiate; Chloroxylenol; Chlortetracycline Bisulfate; Chlortetracycline Hydrochloride; Cinoxacin; Ciprofloxacin; Ciprofloxacin Hydrochloride; Cirolemvcin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodiumr; Nafcillin Sodium; Nalidixate Sodium; Nalidixic Acid; Natainycin; Nebramycin; Neomycin Palmitate; Neomycin Sulfate; Neomycin Undecylenate; Netilmicin Sulfate; Neutramycin; Nifuiradene; Nifuraldezone; Nifuratel; Nifuratrone; Nifurdazil; Nifurimide; Nifiupirinol; Nifurquinazol; Nifurthiazole; Nitrocycline; Nitrofurantoin; Nitromide; Norfloxacin; Novobiocin Sodium; Ofloxacin; Onnetoprim; Oxacillin Sodium Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabainine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallitnycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Suifamethoxazole; Sulfamonomethoxine; Sulfanioxole; Sulfanilate Zinc; Suifanitran; Sulfasalazine; Sulfasomizole; Sulfathiazole; Sulfazamet; Sulfisoxazole; Sulfisoxazole Acetyl; Sulfisboxazole Diolamine; Sulfomyxin; Sulopenem; Sultamricillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Tritnethoprim; Trimethoprim Sulfate; Trisulfapyrimidines; Troleandomycin; Trospectomycin Sulfate; Tyrothricin; Vancomycin; Vancotnycin Hydrochloride; Virginiamycin; or Zorbamycin.

The disclosed compounds can also be combined with foaming agents such as sodium laureth ether sulfate (SLES), sodium lauryl dodecyl sulfate (SDS), disodium laureth sulfosuccinate, ammonium lauryl sulfate (ALS), sodium pareth sulfate, and sodium coceth sulfate. Foaming agents can be present at from about 1% to about 70%, about 5% to about 50%, about 10% to about 30%, or about 1% to about 5% by weight.

The disclosed compounds can, in some examples, further comprise one or more antibiotics. Examples of antibiotics include amikacin, gentamicin, kanamycin, neomycin, streptomycin, tobramycin, bacitracin, clindamycin, daptomycin, lincomycin, linezolid, metronidazole, polymyxin, rifaximin, vancomycin, penicillin, cephalosporin, cephazolin, cephalexin, erythromycin, azithromycin, ciprofloxacin, levofloxacin, sulfadiazine, minocycline, tetracycline, and rifampin. The proportion of antibiotics can be about 0.001% to about 10%, about 0.01% to about 5%, about 0.1% to about 10%, or about 1% to about 5% by weight.

The disclosed compounds can, in some examples, further comprise additional agents such as acyclovir, cephradine, malphalen, procaine, ephedrine, adriamycin, dauno, mycin, plumbagin, atropine, quinine, digoxin, and quinidine, cephradine, cephalothin, cishydroxy-L-proline, melphalan, nicotinic acid, nitric oxide, nitroglycerin, chemodeoxycholic acid, chlorambucil, paclitaxel, sirolimus, 5-flurouracil, paclitaxel, mercaptoethanesulfonate, verapamil, or antifungal agents. The proportion of these additional agents can be about 0.001% to about 10%, about 0.01% to about 5%, about 0.1% to about 10%, or about 1% to about 5% by weight.

In some examples, the disclosed compounds can further comprise anti-inflammatory agents. Examples of such agents include acetaminophen, aspirin, celecoxib, diclofenac, diflunisal, flurbiprofen, ibuprofen, indomethacin, ketoprofen, ketorolac, meclofenamate, meloxicam, methyl salicylate, nabumetone, naproxen, oxaprozin, piroxicam, sulindac, tolmetin, trolamine. The proportion of these anti-inflammatory agents can be present in the formulation at from about 1% to about 70%, about 5% to about 50%, about 10% to about 30%, or about 1% to about 5% by weight.

Administration

The disclosed compounds can be administered either sequentially or simultaneously in separate or combined pharmaceutical formulations. When one or more of the disclosed compounds is used in combination with a second therapeutic agent the dose of each compound can be either the same as or differ from that when the compound is used alone. Appropriate doses will be readily appreciated by those skilled in the art.

The term “administration” and variants thereof (e.g., “administering” a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), “administration” and its variants are each understood to include concurrent and sequential introduction of the compound or prodrug thereof and other agents.

In vivo application of the disclosed compounds, and compositions containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or compositions can be a single administration, or at continuous or distinct intervals as can be readily determined by a person skilled in the art.

The compounds disclosed herein, and compositions comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms, The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The compositions used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The compositions also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Compounds disclosed herein, and compositions comprising them, can be delivered to a cell either through direct contact with the cell or via a carrier means. Carrier means for delivering compounds and compositions to cells are known in the art and include, for example, encapsulating the composition in a liposome moiety. Another means for delivery of compounds and compositions disclosed herein to a cell comprises attaching the compounds to a protein or nucleic acid that is targeted for delivery to the target cell. U.S. Pat. No. 6,960,648 and U.S. Application Publication Nos. 20030032594 and 20020120100 disclose amino acid sequences that can be coupled to another composition and that allows the composition to be translocated across biological membranes. U.S. Application Publication No. 20020035243 also describes compositions for transporting biological moieties across cell membranes for intracellular delivery. Compounds can also be incorporated into polymers, examples of which include poly (D-L lactide-co-glycolide) polymer, poly[bis(p-carboxyphenoxy) propane: sebacic acid] in a 20:80 molar ratio (as used in GLIADEL); chondroitin; chitin; and chitosan.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Unless noted otherwise, air- and/or moisture-sensitive reactions were carried out using oven-dried glassware under an atmosphere of either thy nitrogen or dry argon. Dichloromethane (DCM), toluene, tetrahydrofuran (THF), and N,N-dimethylformamide (DMF) were dried before use by passage through activated alumina under nitrogen atmosphere. Automated flash chromatography on silica gel was performed using a Teledyne-ISCO $^1$H NMR spectra were recorded at 400 MHz using residual protiated solvent as the internal reference: $(CD_3)_2SO$ (2.50 ppm), $CDCl_3$ (7.26 ppm), or $CD_3OD$ (3.31). Assayed compounds had a purity of >90% as determined by $^1$H NMR analysis; spectra are provided in the Supporting information. $^{13}$C NMR spectra were recorded at 100 MHz using the solvent signal as the internal reference: $(CD_3)_2SO$ (39.52 ppm), $CDCl_3$ (77.16 ppm), or $CD_3OD$ (49.00). High-resolution mass spectrometry was performed using electrospray ionization.

Synthesis of NRTIs with Fused Linker Derived From Isomaninide

Isomannide 8 was initially mono-tosylated to provide 9 in a modest yield by reaction with para-toluenesulfonyl chloride in the presence of pyridine (Kumar, S., et al., The Synthesis and Applications of Asymmetric Phase-Transfer Catalysts Derived from Isomannide and isosorbide. *Tetrahedron* 2005, 61, 4141-4148) (Scheme 3). Nucleophilic displacement of the tosylate by potassium phthalimide (Thiyagarajan, S., et al., Chiral Building Blocks from Biomass: 2,5-Diamino-2,5-Dideoxy-1,4,3,6-Dianhydroiditol. *Tetrahedron* 2011, 67, 383-389) introduced the key nitrogen atom in 10. Oxidation of the remaining secondary alcohol was carried out using the Dess-Martin periodinane (Dens, D. B., et al., Readily Accesible 12-1-5 Oxidant for the Conversion of Primary and Secondary Alcohols to Aldehydes and Ketones. *J. Org. Chem.* 1983, 48, 4155-4156) to afford ketone 11. Grignard addition of vinylmagnesium chloride proceeded to afford the tertiary alcohol 12 with high diastereoselectivity. The stereochemistry of intermediate 12 was established unambiguously through X-ray crystallography.

The DNA-binding motif was coupled using a Heck reaction (Beletskaya, I. P., et al., The Heck Reaction as a Sharpening Stone of Palladium Catalysis. *Chem. Rev.* 2000, 100, 3009-3066) to provide 15 and 16. Different conditions were required for the quinoline intermediate 13 and the fluoronaphthyridine intermediate 14. A comprehensive optimization of the Heck reaction was not carried out, and the origins of the differential reactivity have not been determined. Hydrogenation of the alkene afforded the saturated, intermediates 17 and 18, which were deprotected as previously described (Lail, M. S., et al., Process Development for the Synthesis of Monocyclic β-Lactam Core 17. *Org. Process Res. Dev.* 2018, 2.2, 212-218) using excess ethanol amine in refluxing ethyl acetate to yield 19 and 20. Finally, diverse enzyme-binding motifs were introduced by means of reductive amination, affording quinoline analogues 21-23 and fluoronaphthyridine derivatives €, 7, and 24-26. Enzyme-binding motifs were chosen based on structure-activity relationships observed in dioxane-linked NBTIs to facilitate comparison between the two series. In summary, two sub-series of NBTIs have been prepared in eight steps from commercially available materials.

Scheme 3

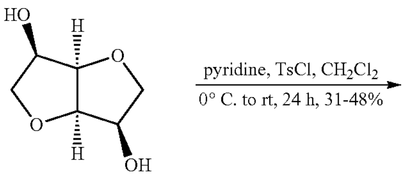

8

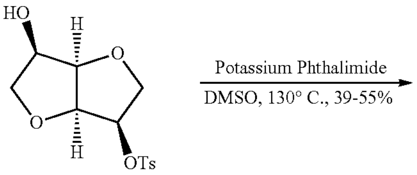

9

-continued

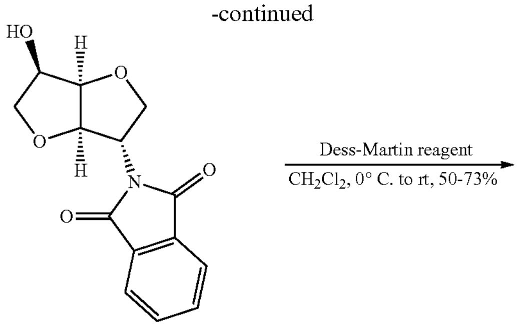

10

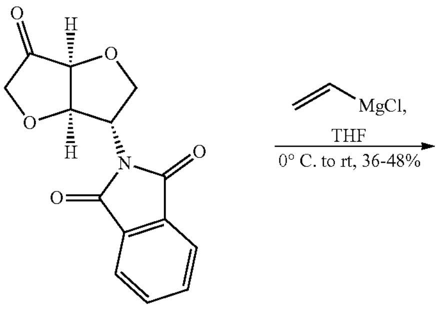

11

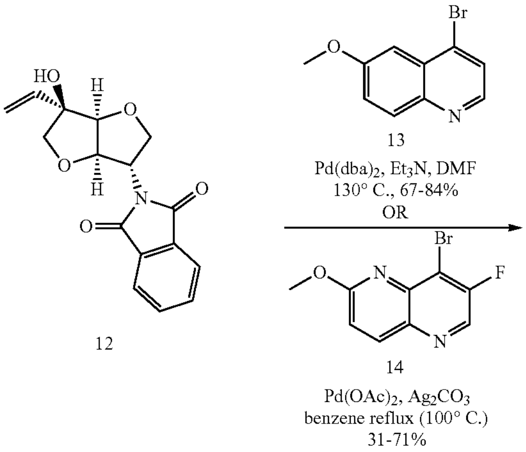

12 13 14

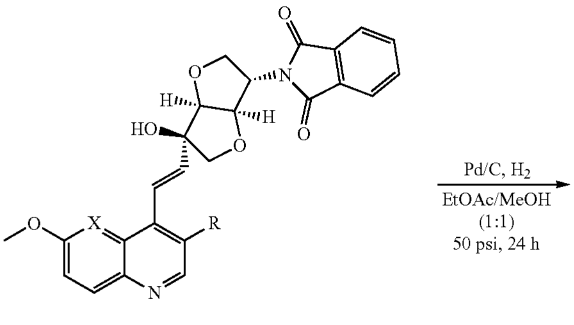

15 (R = H, X = CH)
16 (R = F, X = N)

-continued

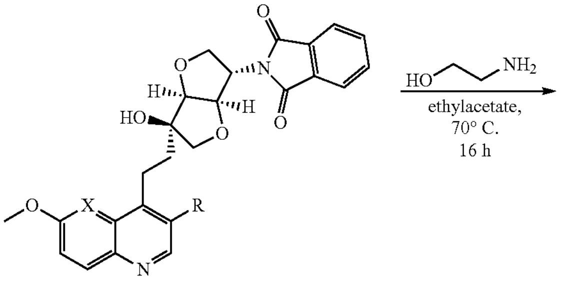

17 (R = H, X = CH):
49-90% yield
18 (R = F, X = N):
66-78% yield

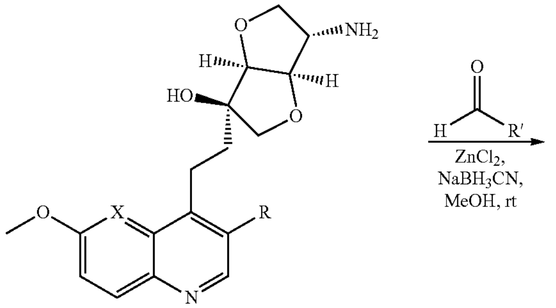

19 (R = H, X = CH):
72-94% yield
20 (R = F, X = N):
91-92% yield

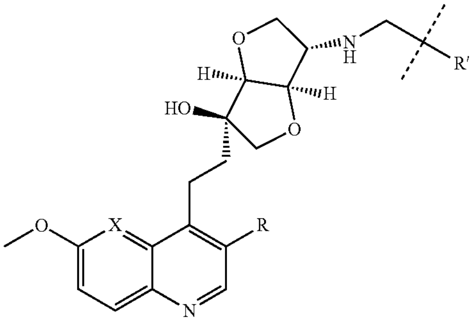

-continued

R = H, X = CH

R' =

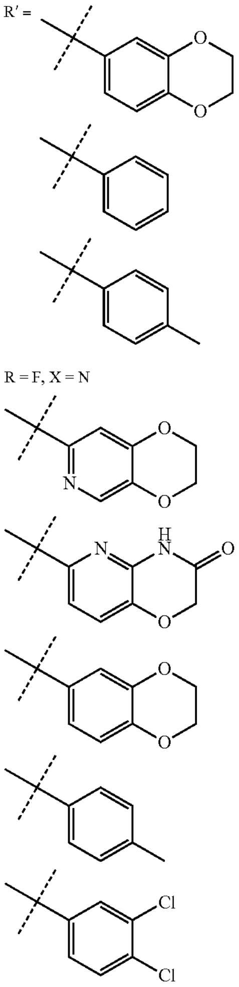

(21)

(22)

(23)

R = F, X = N (6)

(7)

(24)

(25)

(26)

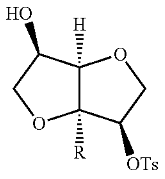

(3R,3aS,6R,6aR)-6-hydroxyhexahydrofuro[3,2-b]furan-3-yl 4-methylbenzenesulfonate (3R,3aS,6R,6aR)-6-hydroxyhexahydrofuro[3,2-b]furan-3-yl methylbenzenesulfonate (9). To a solution of isomannide (8, 15.0 g, 103 mmol, 1.0 equiv) in DCM (51 mL) at 0° C. under nitrogen was added pyridine (16.6 mL, 205 mmol, 2.0 equiv) and p-toluenesulfonyl chloride (22.5 g, 118 nmol, 1.15 equiv). The reaction temperature was gradually raised to room temperature and stirring continued for 24 h. The reaction was diluted with DCM and quenched at 0° C. by addition of 1 N HCl solution. The two layers were separated, and the aqueous phase extracted with DCM (3×50 mL). The combined organic layers were washed with brine, then dried over anhydrous sodium sulfate and concentrated under vacuum. The residue was purified by chromatograghy using 0-10% methanol/DCM to give the title compound as a white solid (11.69 g, 38.99 mmol, 38% yield). This reaction was run eight times under similar conditions with an average yield of 39% (range 30-48%). NMR ($CDCl_3$, 400 MHz): δ 7.79 (d, J=8.3 Hz, 2H), 7.33 (d, J=8.1 Hz, 2H), 4.91-4.83 (m, 1H), 4.45 (t, J=4.9 Hz, 1H), 4.39 (t, J=5.0 Hz, 1H), 4.29-4.21 (m, 1H), 3.97 (dd, J=9.3, 6.5 Hz, 1H), 3.91 (dd, J=9.3, 6.5 Hz, 1H), 3.75 (dd, J=9.3, 7.5 Hz, 1H), 3.51 (dd, J=9.3, 73 Hz, 1H), 2.61 (bs, 1H), 2.42 (s, 3H); $^{13}C$ NMR ($CDCl_3$, 100 MHz): δ 145.3, 133.1, 130.0, 128.0, 81.5, 80.1, 78.5, 73.9, 72.4, 70.1, 21.7, HRMS (ESI) m/z calcd for $C_{13}H_{16}SO_6Na$ $[M+Na]^+$: 323.05653; found: 323.05701.

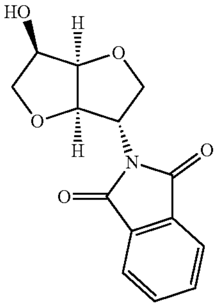

2-((3S,3aR,6R,6aR)-6-hydroxyhexahydrofuro[3,2-b]furan-3-yl)isoindoline-1,3-dione 2-((3S,3aR,6R,6aR)-6hydroxyhexahydrofuro[3,2-b]furan-3-yl)isoindoline-1,3-dione (10). To a solution of 9 (11.2832 g, 37.6019 mmol, 1.0 equiv) in DMSO (67 mL) at room temperature under argon, was added potassium phthalimide (9.0540 g, 48.882 mmol, 1.3 equiv). The reaction mixture was stirred at 130° C. for 16 h, then cooled to room temperature and poured into cold water. The resulting mixture was extracted with DCM (3×50 mL), then the combined organic layers were dried over anhydrous sodium sulfate, filtered, and concentrated under vacuum. The residue was purified by chromatography using 30-70% ethyl acetate/hexanes to give the title compound as a white solid (4.95 g, 18.0 mmol, 48% yield). This reaction was run five times under similar conditions with an average yield of 47% (range 39-55%); the obtained solid was often yellowish in color. $^1H$ NMR. ($CDCl_3$, 400 MHz): δ 7.87-7.80 (m, 2H), 7.76-7.69 (m, 2H), 5.01 (dd, J=4.9, 2.1 Hz, 1H), 4.89 (t, J=5.2 Hz, 1H), 4.87-4.80 (m, 1H), 4.31-4.24 (m, 2H), 4.05 (dd, J=9.3, 6.3 Hz, 1H), 3.91 (dd, J=9.3, 5.9 Hz, 1H), 3.70 (dd, J=9.3, 6.5 Hz, 1H), 2.60 (s, 1H); $^{13}C$ NMR ($CDCl_3$, 100 MHz): δ 167.7, 134.4, 131.7, 123.6, 86.1, 82.9, 72.7, 72.1, 72.0, 57.4; HRMS (ESI) m/z calcd for $C_{14}H_{13}NO_5Na$ $[M+Na]^+$: 298.06914; found: 298.06958.

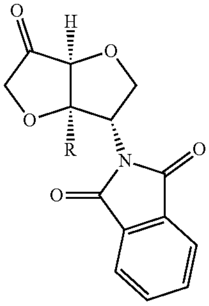

2-((3S,3aR,6R,6aS)-6-oxohexahydrofuro[3,2-b]firam-3-yl)isoindoline-1,3-dione 2-((3S,3aR,6aS)-6-oxotiexahydrofuro[3,2-b]furan-3-yl)isoindoline-1,3-dione (11). To a stirred solution 10 (3.23 g, 11.7 mmol, 1.0 equiv) in DCM (58 mL) at 0° C. was added the Dess-Martin periodinane reagent (9.96 g, 23.5 mmol, 2.0 equiv). After stirring at 0° C. for 15 min, reaction was continued overnight at room temperature, then quenched at 0° C. by addition of a saturated aqueous sodium thiosulfate/sodium bicarbonate solution. The two layers were separated, and the aqueous layer extracted with ethylacetate (3×50 mL). The combined organic layers were washed with brine, then dried over anhydrous sodium sulfate, filtered, and concentrated under reduced pressure. The residue was purified by chromatography with 40-50% ethylacetate/hexanes to give a white solid product (2.33 g, 8.53 mmol, 73% yield). This reaction was run three times under similar conditions with an average yield of 64% (range 50-73%). $^1H$ NMR ($CDCl_3$, 400 MHz): δ 7.90-7.83 (m, 2H), 7.79-7.72 (m, 2H), 5.28 (d, J=4.6 Hz, 1H), 5.06-5.00 (m, 1H), 4.75 (d, J=4.7 Hz, 1H), 4.35 (dd, J=9.5, 7.0 Hz, 1H), 4.28 (d, J=17.4 Hz, 1H), 4.09 (dd, J=9.5, 4.8 Hz, 1H), 4.02 (d, J=17.4 Hz, 1H); $^{13}C$ NMR ($CDCl_3$, 100 MHz): δ 209.8, 167.7, 134.6, 131.6, 123.7, 86.1, 80.7, 73.1, 70.9, 57.7; HRMS (ESI) m/z calcd, for $C_{14}H_{12}NO_5$ $[M+H]^+$: 274.07155; found: 274.07366.

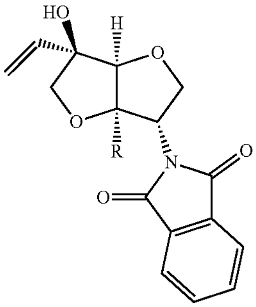

2-((3S,3aR,6R,6aS)-6-hydroxy-6-vinylhexahydrofuro[3,2-b]furan-3-yl)isoindoline-1,3-dione 2-((3S,3aR,6R,6aS)-6-hydroxy-6-vinylhexahydrofuro[3,2-b]furan-3-yl)isoindoline-1,3-dione (12). To a cooled solution (0° C.) of 11 (1.46 g, 5.33 mmol, 1.0 equiv) in THF (10.6 mL) was slowly added vinylmagnesium chloride (4.0 mL, 1.6 M in THF, 6.4 mmol, 1.2 equiv). The reaction was warmed to room temperature and stirred for 16 h, then quenched at 0° C. with saturated $NH_4Cl$ solution. The aqueous layer was extracted with ethyl acetate (3×25 mL), and the combined organic layers were washed with brine, dried over anhydrous sodium sulfate, filtered, and concentrated under vacuum. The residue was purified by chromatography using 30-50% ethylacetatel hexanes to give the title compound as a white solid product (775 mg, 2.57 mmol, 48% yield). This reaction was run three times under similar conditions with an average yield of 43% (range 36-48%). $^1H$ NMR. ($CDCl_3$, 400 MHz): δ 7.88-7.81 (m, 2H), 7.77-7.70 (m, 2H), 5.95 (dd, J=17.3, 10.9 Hz, 1H), 5.49 (dd, J=17.3, 1.2 Hz, 1H), 5.24 (dd, J=10.9, 1.2 Hz, 1H), 5.06 (dd, J=4.9, 2.0 Hz, 1H), 4.90 (ddd, J=7.5, 5.8, 1.8 Hz, 1H), 4.65 (d, J=4.9 Hz, 1H), 4.34 (dd, J=9.3, 7.5 Hz, 1H), 4.07 (dd, J=9.3, 5.9 Hz, 1H), 3.79, 3.78 (ABq, J=9.3 Hz, 2H), 2.97 (s, 111); $^{13}C$ NMR ($CDCl_3$, 100 MHz): δ 167.7, 138.2, 134.5, 131.8, 123.6, 115.2, 87.8, 86.4, 79.7, 76.3, 72.3, 57.5; HRMS (ESI) m/z calcd for $C_{16}H_{15}NO_5Na$ $[M+Na]^+$: 324.08479; found: 324.08545.

X-Ray Crystallography of Compound 12

The sample for X-ray crystallography was prepared as follows: 23.2 mg 12 was dissolved in toluene in a test tube. The test tube was placed in a larger chamber containing pentane. The chamber was covered and allowed to sit undisturbed for three weeks, whereupon crystals were collected.

The data collection crystal was a colorless plate cut from the end of a rod. Examination of the diffraction pattern on a Bruker D8 Venture diffractometer system with a Photon II detector indicated a monoclinic crystal system. All work was done at 150 K using an Oxford Cryosystems Cryostream Cooler. The data collection strategy was set up to measure a quadrant of reciprocal space with a redundancy factor of 6, which means that 90% of the reflections were measured at least 6 times. Omega and phi scans with a frame width of 0.5° and a frame time of 10 seconds were used. The data frames were collected using the program APEX3 and processed with the SAINT program within APEX3. Absorption and beam corrections were made with the multi scan technique in SADABS 9 (Krause, L., et al., SADABS, v2016/2: Bruker AXS Area Detector Scaling and Absorption Correction. J. Appl. Cryst. 2015, 48, 3-10).

The structure was solved by the direct methods procedure in SHELXT (Sheldrick, G. M. SHELXT: Integrated Space-Group and Crystal-Structure Determination. *Acta Crystallogr.* 2015, C71, 3-8) in $P1_1$. Full-matrix least-squares refinements based on $F^2$ were performed in SHELXL-2014/7 (Sheldrick, G. M. SHELXL-2014/7. *Acta Crystallogr.* 2015, C71, 3-8), as incorporated in the WinGX package (Farrugia, L. J. WinGX-Version 2013.3. *J. Appl. Cryst.* 2012, 45, 849-854). The correct enantiomer was chosen based on a known chiral center in the molecule.

The hydroxyl group hydrogen atom was refined isotropically. The remaining hydrogen atoms were added at calculated positions using a riding model with U(H)=1.2*Ueq (bonded carbon atom). The final refinement cycle was based on 3289 intensities and 204 variables and resulted in agreement factors of R1(F)=0.026 and wR2($F^2$)=0.069. For the subset of data with I>2*sigma(I), the R1(F) value is 0.026 for 3261 reflections. The final difference electron density map contains maximum and minimum peak heights of 0.23 and −0.19 e/Å$^3$. Neutral atom scattering factors were used and include terms for anomalous dispersion.

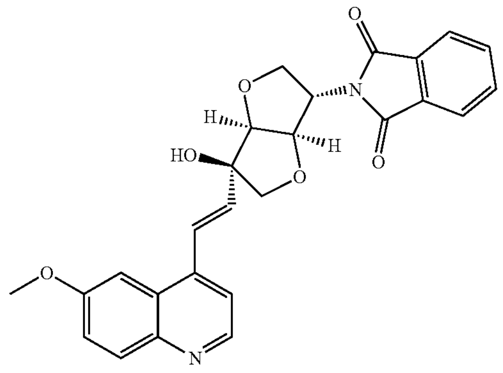

2-((3S,3aR,6R,6aS)-6-hydroxy-6-((E)-2-(6-methoxyquinolin-4-yl)vinyl)hexahydrofuro[3,2-b]furan-3-yl)isoindoline-1,3-dione 2-((3S,3aR,6R,6aS)-6-hydroxy-6-4E)-2-(6-methoxyquinolin-4-yl)vinyl)hexahydrofuro[3,2-b]furan-3-yl)isoindoline-1,3-dione (15). 4-bromo-6-methoxyquinoline (13, 0.6792 g, 2.853 mmol, 1.5 equiv) and 12 (0.5730 g, 1.902 mmol, 0.794 mmol, 1.0 equiv) were dissolved in DNIF (19 mL) under argon. $Pd(dba)_2$ (0.1094 g, 0.1902 mmol, 0.10 equiv) was then added followed by slow addition of trimethylamine (0.80 mL, 5.7 mmol, 3.0 equiv). The reaction was stirred 30 min at room temperature and 24 h at 120° C. After cooling to room temperature, the reaction was quenched by addition of water and the aqueous layer extracted repeatedly with ethyl acetate. The combined organic layers were washed with brine, dried over $Na_2SO_4$, filtered, and concentrated under vacuum. The residue was purified by chromatography (20-80% ethyl acetate in hexanes) to afford the title compound as a yellow solid, contaminated with small impurities (580.3 mg, 1.266 mmol, 67%). This reaction was repeated under similar conditions once with a yield of 84%, although the impurity profile in that case was worse, $^1H$ NMR ($CDCl_3$, 400 MHz): δ 8.72 (d, J=4.6 Hz, 1H), 8.04 (d, J=9.2 Hz, 1H), 7.89-7.83 (m, 2H), 7.79-7.72 (m, 2H), 7.55 (d, J=15.7 Hz, 1H), 7.42 (d, J=4.6 Hz, 1H), 7.39 (dd, J=9.2, 2.7 Hz, 1H), 7.33 (d, J=2.7 Hz, 1H), 6.50 (d, J=15.7 Hz, 1H), 5.19 (dd, J=4.9, 1.9 Hz, 1H), 4.98 (ddd, J=7.4, 5.8, 1.8 Hz, 1H), 4.83 (d, J=4.9 Hz, 1H), 4.43 (dd, J=9.3, 7.5 Hz, 1H), 4.14 (dd, J9.4, 5.8 Hz, 1H), 3.96 (s, 3H), 3.94 (s, 2H), 3.31 (s, 1H).

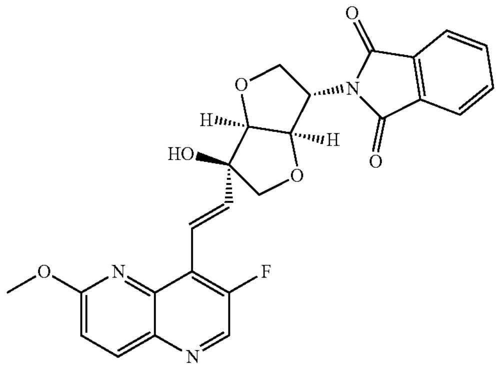

2-((3S,3aR,6R,6aS)-6-((E)-2-(3-fluoro-6-methoxy -1,5-naphthyridin-4-yl)vinyl)-6-hydroxyhexahydrofuro [3,2-b]furan-3-yl)isoindoline-1,3-dione 1-((3S,3aR,6R,6aS)-6-((E)-2-(3-6-methoxy-1,5-naphthyridin-4-yl)vinyl)-6-hydroxyhexahydrofuro[3,2-b]furan-3-yl)isoindoline-1,3-dione (16). A solution of 8-bromo-7-fluoro-2-methoxy-1,5-naphthyridine (14, 200 mg, 0.778 mmol, 1.0 equiv), 12 (240 mg, 0.794 mmol, 1.02 equiv), $Pd(OAc)_2$ (17.4 mg, 77.8 mmol), and $Ag_2CO_3$ (429 mg, 1.56 mmol, 2.0 equiv) in benzene was refluxed at 100° C. under argon for 5 days. The reaction mixture was cooled to room temperature, then diluted with ethyl acetate, and the insoluble material filtered off over celite. After washing the celite with ethyl acetate, solvent was removed from the filtrate under vacuum, and the residue purified by chromatography with 15-50% ethylacetate/hexanes to give the title compound as a white solid product (145 mg, 0.304 mmol, 39% yield). This reaction was run three times under similar conditions (48-120 h at reflux) with an average yield of 47% (range 31-71%). $^1H$ NMR ($CDCl_3$, 400 MHz): δ 8.63 (d, J=2.1 Hz, 1H), 8.15 (d, J=9.0 Hz, 1H), 7.88-7.81 (m, 2H), 7.76-7.70 (m, 2H), 7.67 (d, J=16.4 Hz, 1H), 7.35 (d, J=16.4 Hz, 1H), 7.06 (d, J=9.0 Hz, 1H), 5.19 (dd, J=4.9, 1.9 Hz, 1H), 4.96 (ddd, J=7.5, 5.8, 1.8 HZ, 1H), 4.84 (d, J=4.9 Hz, 1H), 4.40 (dd, J=9.3, 7.5 Hz, 1H), 4.12 (dd, J=9.3, 5.9 Hz, 1H), 4.08 (s, 3H), 3.94 (s, 2H), 3.29 (s, 1H); $^{13}C$ NMR ($CDCl_3$, 100 MHZ): δ 167.7, 162.5, 157.6, 155.0, 140.8, 140.7, 140.4, 140.3, 140.2, 139.03, 139.00, 138.6, 138.3, 134.5, 131.7, 125.03, 124.95, 123.6, 118.1, 115.32, 115.29, 88.0, 86.6, 80.4, 76.6, 72.5, 57.5, 54.2; HRMS (ESI) m/z calcd for $C_{25}H_{20}FN_3O_6Na$ [M+Na]$^+$: 500.12339; found: 500.12531.

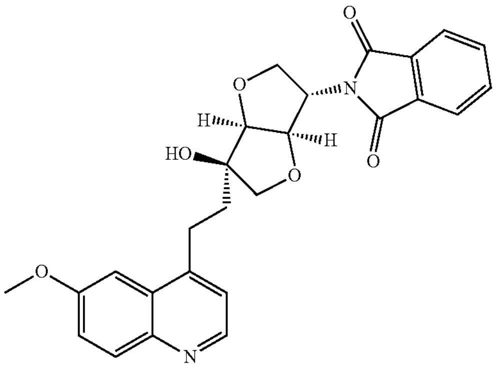

2-((3S,3aR,6R,6aS)-6-hydroxy-6-(2-(6-methoxyquinolin-4-yl)ethyl)hexahydrofuro[3,2-b]furan-3-yl)isoindoline-1,3-dione 2-((3S,3aR,6R,6aS)-6-hydroxy-6-(2-(6-methoxyquinolin-4-yl)ethyl)hexahydrofuro[3,2-b]furan-3-yl)isoindoline-1,3-dione (17). A mixture of 15 (0.3431 g, 0.7484 mmol, 1.0 equiv) and 10% Pd/C (0.080 g) in 1:1 methanol/ethyl acetate (30 mL) was vigorously stirred under 1 atm $H_2$ (balloon) for 48. The mixture was then filtered through celite, washing several times with ethyl acetate, methanol, and DCM. The filtrate was concentrated under reduced pressure and the resulting residue purified by chromatography (2-5% methanol in DCM) to afford the title compound as a yellow solid, contaminated with solvent residues and ca. 5% unreacted starting material (0.2464 g, 0.5351 mmol, 72% yield). This reaction was run three times under similar conditions with an average yield of 70% yield (range 49-90%), but the product was never completely pure. $^1H$ NMR ($CDCl_3$, 400 MHz): δ 8.65 (d, 4.4 Hz, 1H), 8.04-7.98 (m, 1H), 7.86-7.80 (m, 2H), 7.76-7.69 (m, 2H), 7.37-7.32 (m, 2H), 7.22 (d, J=4.5 Hz, 1H), 5.06 (dd, J=4.9, 2.1 Hz, 1H), 4.90 (ddd, J=7.7, 6.6, 2.0 Hz, 1H), 4.65 (d, J=4.9 Hz, 1H), 4.35 (dd, J=9.2, 7.7 Hz, 1H), 4.09 (dd, J=9.3, 6.4 Hz, 1H), 3.94 (s, 3H), 3.81, 3.78 (ABq, J=9.3 Hz, 2H), 3.30-3.15 (m, 3H), 2.12-1.94 (m, 2H); HRMS (ESI) m/z calcd for $C_{16}H_{25}N_2O_6$ [M+H]$^+$: 461.17126; found: 461.17102.

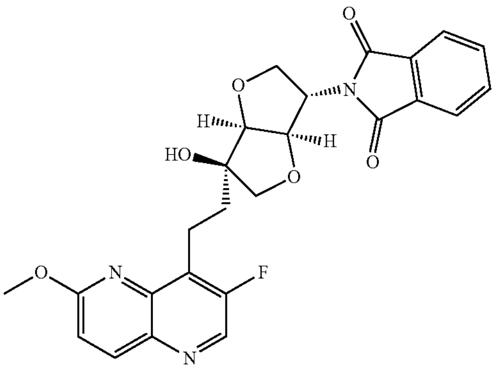

2-((3S,3aR,6R,6aS)-6-(2-(3-fluoro-6-methoxy-1,5-naphthyridin-4-yl)ethyl)-6-hydroxyhexahydrofuro[3,2-b]furan-3-yl)isoindoline-1,3-dione 2-((3S,3aR,6R,6aS)-6-(2-(3-fluoro-6-methoxy-1,5-naphthyridin-4-yl)ethyl)-6-hydroxyhexahydrofuro[3,2-b]furan-3-yl)isoindoline-1,3-dione (18). Compound 16 (145 mg, 0.304 mmol, 1.0 equiv) was dissolved in a 1:1 mixture of ethyl acetate and methanol (12 mL). To the solution was added 10% Pd/C (0.0646 mg), and the mixture was subjected to hydrogenation at 50 psi in a Parr hydrogenator. After 24 h, the reaction mixture was filtered over celite, and then washed with ethyl acetate and methanol. The filtrate was concentrated under reduced pressure, and the crude product was purified by chromatography with 20-50% ethyl acetate hexanes to give the title compound as a whitish solid (95.4 mg, 0.199 mmol, 66% yield, contaminated with ethyl acetate). This reaction was run three times under similar conditions with an average yield of 70% (range 66-78%). $^1H$ NMR ($CDCl_3$, 400 MHz): δ 8.61 (s, 1H), 8.16 (d, J=9.0 Hz, 1H), 7.87-7.81 (m, 2H), 7.77-7.70 (m, 2H), 7.06 (d, J=9.0 Hz, 1H), 5.04 (dd, J5.0, 2.1 Hz, 1H), 4.92-4.86 (m, 1H), 4.72 (d, J=5.0 Hz, 1H), 4.34 (dd, J=9.2, 7.6 Hz, 1H), 4.11 (s, 3H), 4.07 (dd, J9.3, 6.3 Hz, 1H), 3.82 (s, 2H), 3.46-3.30 (in, 2H), 3.13 (s, 1H), 2.10-1.92 (m, 2H); $^{13}C$ NMR ($CDCl_3$, 100 MHz): δ 167.7, 162.6, 158.4, 155.8, 141.6, 141.5, 140.3, 138.62, 138.60, 138.2, 137.9, 134.5, 132.1, 131.9, 131.8, 123.6, 115.43, 115.40, 86.9, 86.2, 79.6, 76.2, 72.0, 57.4, 54.1, 35.5, 18.0, 17.9; HRMS (ESI) calcd for $C_{25}H_{22}FN_3O_6Na$ [M+Na]$^+$: 502.13904; found: 502.13925.

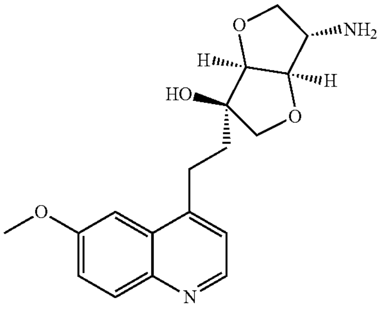

(3R,3aS,6S,6aR)-6-amino-3-(2-(6-methoxyquinolin-4-yl)ethyl) hexahydrofuro[3,2-b]furan-3-ol (3R,3aS,6S,6aR)-6-amino-3-(2-(6-methoxyquinolim-4-yl)ethyl)hexahydrofuro[3,2-b]furan-3-ol (19). Compound 17 (0.1530 g, 0.3323 mmol, 1.0 equiv) and ethanolamine (0.30 mL, 5.0 mmol, 15 equiv) were combined in ethyl acetate and stirred at 70° C. for 16 h. Ethyl acetate was removed under vacuum, and the residue was dissolved in DCM and washed with brine. The aqueous layer was extracted with DCM, and the combined organic layers were dried over $Na_2SO_4$, filtered, and concentrated under vacuum. The resulting residue was purified by chromatography (0-8% methanol in DCM) to afford the title compound as a thick, clear oil (0.0867 g, 0.262 mmol, 79%, contaminated with small amount methanol). This reaction was run two additional times under similar conditions with yields of 72% and 94%, but the products were not completely pure. $^1$H NMR ($CD_3OD$, 400 MHz): δ 8.55 (d, J=4.5 Hz, 1H), 7.91 (d, J=9.2 Hz, 1H), 7.45 (d, J=2.7 Hz, 1H), 7.39 (dd, J=9.2, 2.6 Hz, 1H), 7.36 (d, J4.6 Hz, 1H), 4.37 (s, 2H), 4.06 (dd, J=9.3, 4.5 Hz, 1H), 3.96 (s, 3H), 3.79 (dd, J=9.3, 1.7 Hz, 1H), 3.75 (d, J=9.2 Hz, 1H), 3.66 (d, J=9.2 Hz, 1H), 3.50 (dd, J=4.4, 1.7 Hz, 1H), 3.30-3.17 (m, 2H), 2.02-1.89 (m, 2H); HRMS (ESI) calcd for $C_{18}H_{23}N_2O_4$ $[M+H]^+$: 331.16578; found: 331.16589.

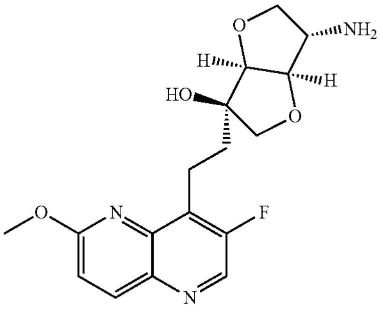

(3R,3aS,6S,6aR)-6-amino-3-(2-(3-fluoro -6-methoxy-1,5-naphthyridin-4-yl) ethyl)hexahydrofuro[3,2-b]furan-3-ol (3R,3aS,6S,6aR)-6-amino-3-(2-(3-fluoro-6-methoxy-1,5-naphthyridin-4-yl)ethyl)hexahydrofuro[3,2-b]furan-3-ol (20). To a solution of 18 (118.4 mg, 0.2469 mmol, 1.0 equiv) in ethyl acetate (8.3 mL), in a flask fitted with a reflux condenser, was added ethanolamine (220 μL, 3.6 mmol, 15 equiv). The reaction was stirred at 70° C. for 24 h. After cooling to room temperature, ethyl acetate was removed under vacuum, and then the residue was dissolved in DCM, and washed with brine. The two lavers were separated, and then aqueous layer was extracted with DCM (3×10 mL). Combined organic layers were dried over anhydrous $Na_2SO_4$, and then filtered, and concentrated under vacuum. The residue was purified by chromatography with 0-10% methanol/DCM to give the title compound (78.7 mg, 0.225 mmol, 91%) as a whitish solid. This reaction was run three times under similar conditions with an average yield of 91% (range 91-92%). $^1$H NMR ($CDCl_3$, 400 MHz): δ 8.58 (s, 1H), 8.14 (d, J=9.0 Hz, 1H), 7.03 (d, J=9.0 Hz, 1H), 4.37 (d, J=4.4 Hz, 1H), 4.25 (d, J=4.4 Hz, 1H), 4.06 (s, 3H), 3.99 (dd, J=9.1, 4.2 Hz, 1H), 3.77 (br d, J=9.1 Hz, 1H), 3.76 (d, J=9.3 Hz, 1H), 3.67 (d, J=9.3 Hz, 1H), 3.59 (br d, J=3.6 Hz, 1H), 1H), 3.41-3.25 (m, 2H), 2.06-1.83 (m, 2H); $^{13}$C NMR ($CDCl_3$, 100 MHz): δ 162.5, 158.3, 155.8, 141.5, 141.4, 140.3, 138.60, 138.58, 138.1, 137.8, 132.0, 131.9, 115.35, 115.32, 89.9, 85.8, 79.9, 77.1, 76.1, 58.6, 53.9, 36.1, 17.99, 17.97; HRMS (ESI) m/z calcd for $C_{17}H_{21}FN_3O_4$ $[M+H]^+$: 350.15610; found: 350.15143.

General Reductive Amination Procedure

Reductive amination to synthesize compounds 21-23 (from amine 19) and compounds 6, 7, and 24-26 (from amine 20) was carried out as follows: The amine (1.0 equiv) and the requisite aldehyde (1.2 equiv) were combined in DCM (0.05 M), and $ZnCl_2$ (0.2 equiv) was added. The reaction was stirred 1 h, whereupon $NaBH_3CN$ (3.0 equiv) was added (effervescence observed). The reaction was stirred overnight, methanol was removed in vacuo, and the residue was dissolved in DCM and washed with brine. The aqueous layer was extracted with DCM, and the combined organic layers were dried over $Na_2SO_4$ and concentrated in vacuo. The crude product was dissolved in DCM, concentrated onto silica gel, and purified by flash chromatography on silica gel using a gradient elution (0 to 5 or 10% methanol in DCM). Concentration in vacuo afforded the reported compounds.

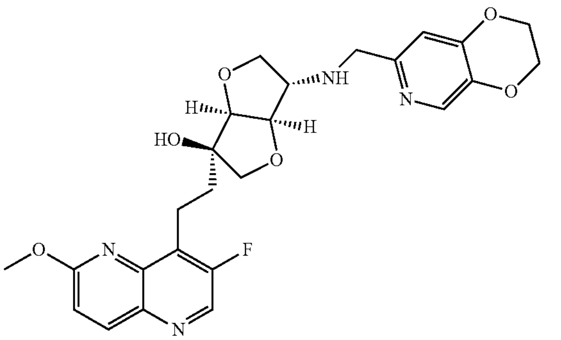

(3R,3aS,6S,6aR)-6-(((2-3-dihydro-[1,4]dioxino [2,3-c]pyridin-7-yl)methyl)amino)-3-(2-(3-fluoro -6-methoxy-1,5-naphthyridin-4-yl)ethyl) hexahydrofuro[3,2-b]furan-3-ol (3R,3aS,6S,6aR)-6-(((2,3-dihydro-[1,4]dioxino[2,36-c] pyridin-7-yl)methyl)amnino)-3-(2-(3-fluoro-6-methoxy-1, 5-naphthyridin-4-yl)ethyl)hexahydrofuro[3,2-b]furan-3-ol (6). From 20 according to the general reductive amination procedure with 2,3-dihydro[1,4]dioxino[2,3-c]pyridine-7-carbaldehyde (Yield 39.4 mg, 79.0 μmol, 64.0%). $^1$H NMR ($CD_3OD$, 400 MHz): δ 8.58 (d, J=0.6 Hz, 1H), 8.14 (d, J=9.1 Hz, 1H), 7.97 (s, 1H), 7.11 (d, J=9.1 Hz, 1H), 6.94 (s, 1H), 4.45 (br d, J=4.6 Hz, 1H), 4.37-4.32 (m, 3H), 4.29-4.25 (m, 2H), 4.08 (s, 3H), 4.02 (dd, J=9.4, 4.9 Hz, 1H), 3.84 (dd, J=9.4, 2.6 Hz, 1H), 3.79 (d, J=9.0 Hz, 1H), 3.76, 3.75 (ABq, J=14.5 Hz, 2H), 3.64 (d, J9.0 Hz, 1H), 3.39-3.24 (m, 3H, overlaps with solvent signal), 1.99-1.81 (m, 2H); $^{13}C$ NMR ($CD_3OD$, 100 MHz): δ 164.1, 159.6, 157.0, 153.7, 152.5, 142.7, 142.6, 142.1, 140.6, 139.43, 139.41, 139.0, 138.8, 138.5, 134.1, 134.0, 116.8, 116.7, 112.4, 88.6, 87.2, 81.1, 76.4, 74.4, 66.5, 66.0, 65.4, 54.6, 52.9, 37.1, 18.90, 18.88; HRMS (ESI) mlz calcd for $C_{25}H_{28}FN_4O_6$ $[M+H]^+$: 499.19929; Found: 499.19910.

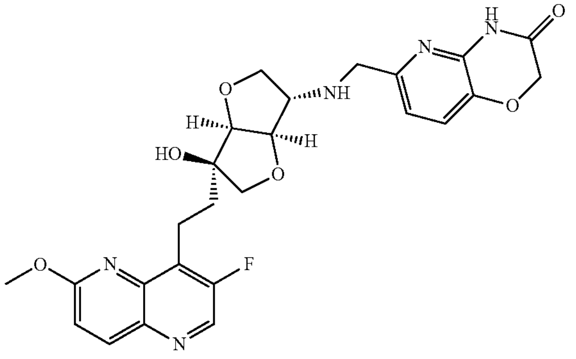

6-((((3S,3aR,6R,6aS)-6-(2-(3-fluoro-6-methoxy-1,5-naphthyridin-4-yl)ethyl)-6-hydroxyhexahydrofuro[3,2-b]furan-3-yl)amino)methyl)-2H-pyrido[3,2-b][1,4]oxazin-3(4H)-one 6-((((3S,3aR,6R,6aS)-6-(2-(3-fluoro-6-methoxy-1,5-tnaphthyriditn-4-yl)ethyl)-6-hydroxyhexahydrofuro[3,2-b]furan-3-yl)amino)methyl)-2H-pyrido[3,2-b][1,4]oxazin-3(4H)-one (7). From 20 according to the general reductive amination procedure with 3-oxo-3,4-dihydro-2H-pyrido[3,2-b][1,4]oxazine-6-carbaldehyde (Yield 33.8 mg, 66.1 μmol, 62.2%). $^1H$ NMR ($[CD_3]_2SO$, 400 MHz): δ 11.16 (s, 1H), 8.76 (s, 1H), 8.27 (d, J=9.0 Hz, 1H), 7.30 (d, J=8.1 Hz, 1H), 7.23 (d, J=9.0 Hz, 1H), 7.00 (d, J=8.1 Hz, 1H), 4.65 (s, 4.60 (s, 2H), 4.36 (br d, J=4.3 Hz, 1H), 4.19 (d, J=4.4 Hz, 1H), 4.04 (s, 3H), 3.88 (dd, J=9.1, 4.8 Hz, 1H), 3.73 (dd, J=9.1, 2.0 Hz, 1H), 3.71-3.64 (m, 3H), 3.49 (d, J=8.6 Hz, 1H), 3.27-3.15 (m, 3H), 1.86-1.70 (m, 2H); $^{13}C$ NMR ($[CD_3]_2SO$, 100 MHz): δ 165.8, 162.0, 157.7, 155.1, 140.78, 140.76, 140.7, 140.4, 138.13, 138.11, 138.07, 137.8, 137.6, 131.7, 131.6, 123.3, 116.8, 115.30, 115.28, 86.6, 85.3, 79.4, 74.2, 72.9, 66.7, 64.7, 53.3, 51.6, 35.7, 17.5; HRMS (ESI) m/z calcd for $C_{25}H_{27}FN_5O_6$ $[M+H]^+$: 512.19454; Found: 512.19489.

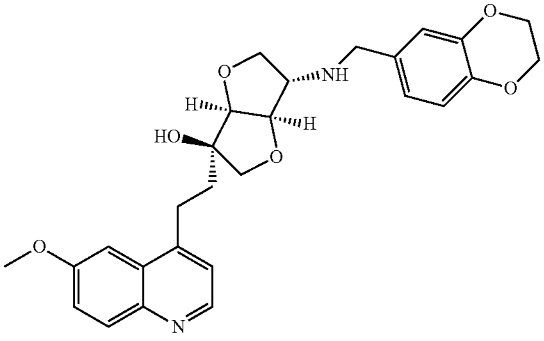

(3R,3aS,6S,6aR)-6-(((2,3-dihydrobenzo[b][1,4]dioxin-6-yl)methyl)amino)-3-(2-(6-methoxyquinolin-4-yl)ethyl)hexahydrofuro[3,2-b]furan-3-ol (3R,3aS,6S,6aR)-6-(((2,3-dihydrobenzo[b][1,4]dioxin-6-yl)methyl)amino)-3-(2-(6-methoxyquinalin-4-yl)ethyl)hexahydrofuro[3,2-b]furan-3-ol (21). From 19 according to the general reductive amination procedure with 2,3-dihydrobenzo[b][1,4]dioxine-6-carbaldehyde (Yield 28.9 mg, 60.4 mmol, 66.5%). $^1H$ NMR ($CD_3OD$, 400 MHz): δ 8.55 (d, J=4.5 Hz, 1H), 7.91 (d, J=9.2 Hz, 1H), 7.46 (d, J=2.7 Hz, 1H), 7.39 (dd, J9.2, 2.7 Hz, 1H), 7.36 (d, J=4.6 Hz, 1H), 6.86-6.74 (m, 3H), 4.48 (dd, J=4.7, 1.0 Hz, 1H), 4.32 (d, J=4.8 Hz, 1H), 4.22-4.17 (m, 4H), 4.05 (dd, J=9.4, 5.2 Hz, 1H), 3.96 (s, 3H), 3.81 (dd, J=9.4, 3.2 Hz, 1H), 3.74 (d, J=9.1 Hz, 1H), 3.68, 3.65 (ABq, J=13.2 Hz, 2H), 3.66 (d, J=9.4 Hz, 1H), 3.28-3.19 (m, 2H), 2.03-1.88 (m, 2H); $^{13}C$ NMR ($CD_3OD$, 100 MHz): δ 159.6, 149.7, 148.2, 145.0, 144.7, 144.3, 133.5, 131.2, 129.9, 123.3, 122.6, 122.3, 118.4, 118.1, 102.9, 88.6, 87.1, 81.0, 76.2, 74.4, 66.7, 65.60, 65.58, 56.2, 52.1, 37.9, 27.4; HRMS (ESI) m/z calcd for $C_{27}H_{31}N_2O_6$ $[M+H]^+$: 479.21821; Found: 479.21719.

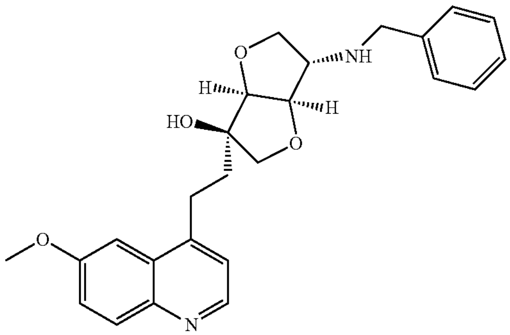

(3R,3aS,6S,6aR)-6-(benzylamino)-3-(2-(6-methoxyquinolin-4-yl)ethyl)hexahydrofuro[3,2-b]furan-3-ol (3R,3aS,6S,6aR)-6-(benzylamino)-3-(2-(6-methoxyquinolin-4-yl)ethyl)hexahydrofuro[3,2-b]furan-3-ol (22). From 19 according to the general reductive animation procedure with benzaldehyde (Yield 20.3 mg, 48.3 mmol, 59.1%). $^1H$ NMR ($CD_3OD$, 400 MHz): δ 8.56 (d, J=4.5 Hz, 1H), 7.91 (d, J=9.2 Hz, 1H), 7.47 (d, J=2.7 Hz, 1H), 7.40 (dd, J=9.2, 2.7 Hz, 1H), 7.38-7.29 (m, 5H), 7.27-7.22 (m, 1H), 4.51 (dd, J=4.8, 0.9 Hz, 1H), 4.33 (d, J=4.8 Hz, 1H), 4.06 (dd, J=9.4, 5.2 Hz, 1H), 3.96 (s, 3H), 3.84 (dd, J=9.4, 3.2 Hz, 1H), δ 3.81, 3.78 (ABq, J=13.0 Hz, 2H), 3.75 (d, J=9.1 Hz, 1H), 3.67 (d, J=9.1 Hz, 1H), 3.36, 3.30 (m, 1H, partially obscured by solvent), 3.29-3.18 (m, 2H), 2.03-1.89 (m, 2H); $^{13}C$ NMR ($CD_3OD$, 100 MHz): δ 159.6, 149.7, 148.2, 144.7, 140.5, 131.2, 129.9, 129.7, 129.5, 128.3, 123.3, 122.3, 102.9, 88.6, 87.1, 81.0, 76.2, 74.5, 65.9, 56.2, 52.7, 38.0, 27.4; HRMS (ESI) calcd for $C_{25}H_{29}N_2O_4$ $[M+H]^+$: 421.21273; Found: 421.21207.

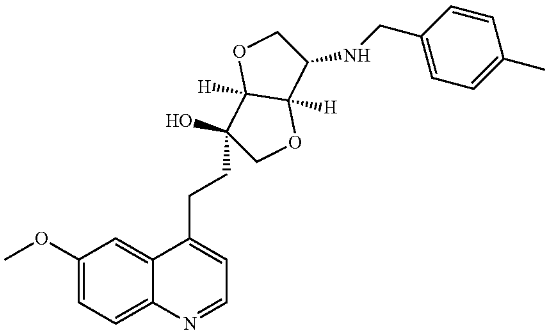

(3R,3aS,6S,6aR)-3-(2-(6
-methoxyquinolin-4-yl)ethyl)
-6-((4-methylbenzyl)amino)
hexahydrofuro[3,2-b]furan-3-ol (3R,3aS,6S,6aR)-3-(2-(6-methoxyquinolin-4-yl)ethyl)-6-((4-methylbenzyl)amino)hexahydrofuro[3,2-h]furan-3-ol (23). From 19 according to the general reductive amination procedure with 4-methylbenzaldehyde (Yield 26.7 mg, 61.4 mmol, 70.1%). $^{1}$H NMR ($CD_3OD$, 400 MHz): δ 8.55 (d, J=4.5 Hz, 1H), 7.91 (d, J=9.2 Hz, 1H), 7.45 (d, J=2.7 Hz, 1H), 7.39 (dd, J=9.2, 2.7 Hz, 1H), 7.35 (d, J=4.6 Hz, 1H), 7.24-7.19 (m, 2H), 7.15-7.10 (m, 2H), 4.49 (dd, J=4.8, 1.3 Hz, 1H), 4.32 (d, J=4.8 Hz, 1H), 4.05 (dd, J=9.4, 5.2 Hz, 1H), 3.95 (s, 3H), 3.82 (dd, J=9.4, 3.2 Hz, 1H), 3.76, 3.72 (ABq, J=12.9 Hz, 2H), 3.74 (d, J=8.9 Hz, 1H), 3.66 (d, J=9.1 Hz, 1H), 3.34-3.30 (m, 1H, partially obscured by solvent), 3.29-3.16 (m, 2H), 2.29 (s, 3H), 2.01-1.88 (m, 2H); $^{13}$C NMR ($CD_3OD$, 100 MHz): δ 159.6, 149.7, 148.2, 144.7, 138.0, 137.3, 131.2, 130.1, 129.9, 129.6, 123.3, 122.3, 102.9, 88.6, 87.1, 81.0, 76.2, 74.5, 65.8, 56.2, 52.4, 37.9, 27.3, 21.1; HRMS (ESI) m/z calcd for $C_{26}H_{31}N_2O_4$ $[M+H]^+$: 435.22838; Found: 435.22787.

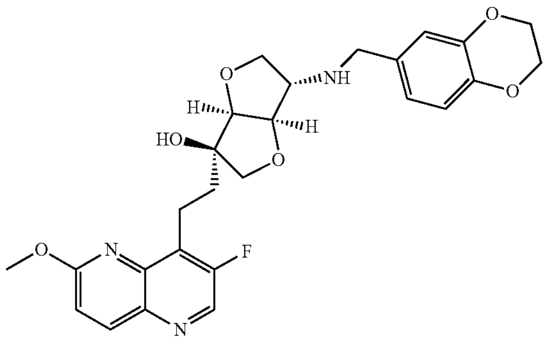

(3R,3aS,6S,6aR)-6-(((2,3-dihydrobenzo
[b][1,4]dioxin-6-yl)methyl)amino)-
3-(2-(3-fluoro-6-methoxy-1,5-naphthyridin
-4-yl)ethyl)hexahydrofuro[3,2-b]furan-3-ol (3R,3aS,6S,6aR)-6-(((2,3-dihydrobenzo[b][1,4]dioxin-6-yl)methyl)amino)-3-(2-(3-fluoro-6-methoxy-1,5-naphthyridin-4-yl)ethyl)hexahydrofuro[3,2-b]furan-3-ol (24). From 20 according to the general reductive amination procedure with 2,3-dihydrobenzo[b][1,4]dioxine-6-carbaldehyde (Yield 43.7 mg, 87.8 μmol, 84.5%). $^{1}$H NMR ($CD_3OD$, 400 MHz): δ 8.57 (d, J=0.9 Hz, 1H), 8.13 (d, J=9.1 Hz, 1H), 7.10 (d, J=9.1 Hz, 1H), 6.82-6.71 (m, 3H), 4.43 (dd, J=4.7, 0.8 Hz, 1H), 4.32 (d, J=4.8 Hz, 1H), 4.21-4.15 (m, 4H), 4.08 (s, 3H), 4.01 (dd, J=9.4, 5.1 Hz, 1H), 3.82-3.76 (m, 2H), 3.68-3.59 (m, 3H), 3.38-3.23 (m, 3H, overlaps with solvent signal), 1.98-1.80 (m, 2H), small amount DCM present; $^{13}$C NMR ($CD_3OD$, 100 MHz): δ 164.1, 159.6, 157.0, 144.9, 144.2, 142.7, 142.6, 140.6, 139.40, 139.38, 138.8, 138.5, 134.1, 134.0, 133.5, 122.5, 118.4, 118.1, 116.8, 116.7, 88.6, 87.2, 81.1, 76.3, 74.3, 65.7, 65.6, 65.5, 54.6, 52.0, 37.1, 18.89, 18.87; HRMS m/z calcd for $C_{26}H_{29}FN_3O_6$ $[M+H]^+$: 498.20404; Found: 498.20401.

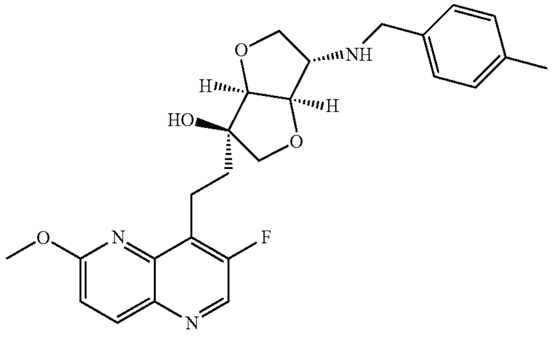

(3R,3aS,6S,6aR)-3-(2-(3-fluoro-6-methoxy
-1,5-naphthyridin-4-yl)ethyl)-6-
((4-methylbenzyl)amino)
hexahydrofuro[3,2-b]furan-3-ol (3R,3aS,6S,6aR)-3-(2-(3-fluora-6-methoxy-1,5-naphthyridin-4-yl)ethyl)-6-((4-methyllbenzyl)amino)hexahydrofuro[3,2-b]furan-3-ol (25). From 20 according to the general reductive amination procedure with 4-methylbenzaldehyde (Yield 32.6 mg, 71.9 μmol, 82.3%). $^{1}$H NMR ($CDCl_3$, 400 MHz): δ 8.61 (d, J=0.5 Hz, 1H), 8.17 (d, J=9.0 Hz, 1H), 7.19 (d, J=8.0 Hz, 2H), 7.13 (d, J=7.9 Hz, 2H), 7.06 (d, J=9.0 Hz, 1H), 4.43 (br d, J=4.6 Hz, 1H), 4.38 (d, J=4.7 Hz, 1H), 4.08 (s, 3H), 4.02 (dd, J=9.3, 4.7 Hz, 1H), 3.87 (dd, J=9.2, 2.2 Hz, 1H), 3.82-3.74 (m, 2H), 3.78 (d, J=9.3 Hz, 1H), 3.71 (d, J=9.3 Hz, 1H), 3.46-3.41 (m, 1H), 3.41-3.27 (m, 2H), 2.32 (s, 3H), 2.05-1.87 (m, 2H); $^{13}$C NMR ($CDCl_3$, 100 MHz): δ 162.6, 158.4, 155.8, 141.6, 141.5, 140.3, 138.7, 138.6, 138.2, 137.9, 137.0, 136.6, 132.1, 132.0, 129.4, 128.2, 115.39, 115.36, 87.6, 86.0, 79.8, 77.1, 74.1, 64.7, 54.0, 51.9, 36.1, 21.2, 18.05, 18.03; HRMS (ESI) m/z caled for $C_{25}H_{29}FN_3O_4$ $[M+H]^+$: 454.21421; Found: 454.21484.

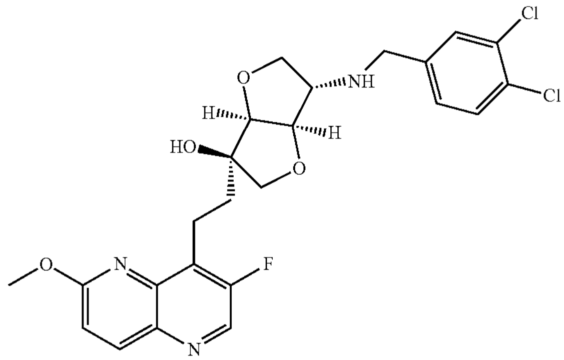

(3R,3aS,6S,6aR)-6-((3,4-dichlorobenzyl)amino)
-3-(2-(3-fluoro-6-methoxy-1,5-naphthyridin
-4-yl)ethyl)hexahydrofuro[3,2-b]furan-3-ol (3R,3aS,6S,6aR)-6-((3,4-dichlorobenzyl)amino)-3-(2-(3-fluoro-6-methoxy-1,5-napkthyridin-4-yl)ethyl)hexahydrofuro[3,2-b]-furan-3-ol (26). From 20 according to the general reductive amination procedure with 3,4-dichlorobenzaldehyde (Yield 38.2 mg, 75.1 μmol, 92.1%), $^1$H NMR ($CDCl_3$, 400 MHz): δ 8.60 (s, 1H), 8.16 (d, J=9.0 Hz, 1H), 7.42. (d, J=1.9 Hz, 1H), 7.37 (d, J=8.2 Hz, 1H), 7.14 (dd, J=8.2, 2.0 Hz, 1H), 7.06 (d, J=9.0 Hz, 1H), 4.41 (br d, J=4.6 Hz, 1H), 4.36 (d, J=4.7 Hz, 1H), 4.08 (s, 3H), 4.02 (dd, J=9.3, 4.7 Hz, 1H), 3.85 (dd, J=9.3, 2.2. Hz, 1H), 3.82-3.74 (m, 2H), 3.78 (d, J=9.4 Hz, 1H), 3.71 (d, J=9.4 Hz, 1.14), 3.42-3.37 (m, 1H), 3.37-3.27 (m, 2H), 2.06-1.85 (m, 2H); $^{13}$C NMR ($CDCl_3$, 100 MHz): δ 162.6, 158.4, 155.8, 141.6, 141.5, 140.4, 140.0, 138.67, 138.65, 138.2, 137.9, 132.7, 132.0, 131.9, 131.3, 130.5, 130.0, 127.4, 115.41, 115.39, 87.5, 86.1, 79.8, 77.1, 73.9, 64.8, 54.0, 50.9, 36.1, 18.03, 18.01; HRMS (ESI) m/z calcd for $C_{24}H_{25}Cl_2FN_3O_4$ $[M+H]^{30}$: 508.12062; Found: 508.12082.

Antibacterial Activity

Minimum inhibitory concentrations (MICs) were determined in triplicate according to Clinical and Laboratory Standards Institute (CLSI) guidelines using one or more strains of *S. aureus*. Strain ATCC 29213 was used for initial evaluation, and ciprofloxacin was employed as a positive control in each assay. Compounds were also assayed using a USA300 (Hidroa, A. I., et al., Emergence of Community-Acquired Meticillin-Resistant *Staphylococcus aureus* Strain USA300 as a Cause of Necrotising Community-Onset Pneumonia. *Lance Infect. Dis.* 2009, 9, 384-392) isolate of MRSA as well as a *S. aureus* strain isolated from a cystic fibrosis patient, using vancomycin as a positive control. Finally, the breadth of antibacterial activity against Gram-positive pathogens was assessed using one representative compound.

Due to their novel binding mode, NBTIs are expected to preserve activity against fluoroquinolone-resistant strains. This assumption was evaluated for this series of isomannide-derived NBTIs: the MICs against the ciprofloxacin-resistant USA300 strain were essentially identical to those against the ciprofloxacin-sensitive ATCC strain. The compounds also demonstrated equivalent MICs against a *S. aureus* isolate from a CF patient, further demonstrating their promising activity.

TABLE 1

Antistaphylococcal activity[a] of isomannide-derived NBTIs and reference compounds.

| Cmpd | Linker | DNA-binding moiety | ATCC 29213 | USA300 | CF isolate |
|---|---|---|---|---|---|
| 4* | Dioxane | quinoline | 0.25-1 | 0.5 | 0.5 |
| 21 | isomannide | quinoline | 16-32 | 16 | 16 |
| 22 | isomannide | quinoline | >8 | >8 | >8 |
| 23 | isomannide | quinoline | >8 | >8 | >8 |
| 27 | Dioxane | fluoronaphthyridine | ≤0.25 | 0.125-0.25 | 0.25 |
| 6 | isomannide | fluoronaphthyridine | 1-4 | 2 | 2 |
| 7 | isomannide | fluoronaphthyridine | 2 | 1-2 | 2 |
| 24 | isomannide | fluoronaphthyridine | 0.5-1 | 1 | 1 |
| 25 | isomannide | fluoronaphthyridine | 1-2 | 2 | 2 |
| 26 | isomannide | fluoronaphthyridine | ≤0.25-0.5 | 0.5 | 0.5 |
| ciprofloxacin | NA[b] | NA | 0.25-0.5 | 16-32 | 0.25 |
| vancomycin | NA | NA | NT | 1-2 | 1-2 |

*4 is the same as compound 9 from Li, L., et al., Synthesis and Anti-Staphylococcal activity of Novel Bacterial Topoisomerase Inhibitors with a 5-Amino-1,3-Dioxane Linker Moiety. Bioorg. Med. Chem. Lett. 2018, 28, 2477-2480

[a]MICs determined according to CLSI broth microdilution guidelines, all values in μg/mL.

[b]NA, not applicable

MIC values for compound 6 were determined against a variety of relevant Gram-positive and Gram-negative pathogens. The data are summarized in Table 2; previously published data for 27 and ciprofloxacin are included for comparison. Using a panel of fluoroquinolone-resistant MRSA isolates, the $MIC_{90}$ of 6 was 16-fold better than that of ciprofloxacin (2 vs. 32 μg/mL, respectively). In summary, isomannide-linked NBTIs offer promising whole cell antibacterial activity against representative pathogens, including fluoroquinolone-resistant isolates.

TABLE 2

Minimum inhibitory concentrations[a] of 6 against representative Gram-positive and Gram-negative bacteria.

| Strain | Cmpd. 6 MIC | Cmpd. 27 MIC | Ciprofloxacin MIC |
|---|---|---|---|
| *S. aureus* ATCC 29213 (n = 3) | 0.25[b] | ≤0.06[b] | 0.25 |
| MRSADRL-3161 | 1 | ≤0.06 | >64 |
| *Streptococcus pyogenes* LSI-1235 | ≤0.12 | ≤0.06 | 0.25 |
| *Streptococcus pneumoniae* LSI-4234[c] | ≤0.12 | 0.25 | 2 |
| *Streptococcus pneumoniae* LSI-4246[d] | ≤0.12 | ≤0.06 | 0.5 |
| *Enterococcus faecium* DRL-4193[e] | 2 | 0.12[f] | 0.25 |
| *Enterococcus faecium* LSI-3340[g] | 0.25 | 0.12 | 16 |
| *Enterococcus faecalis* ATCC 29212 | 2 | 0.5 | 0.5 |
| Fluoroquinolone-resistant *S. aureus* $MIC_{90}$ (11 strains) | 2 | NT | 32 |
| *Escherichia coli* ATCC 25922 (n = 2) | 64 | 16 | ≤0.06 |
| *Pseudomonas aeruginosa* LSI-2946 | ≤0.12 | 4 | 0.5 |
| *Acinetobacter baumannii* LSI-2957 | ≤0.12 | 2 | 0.25 |
| *Klebsiella pneumoniae* LSI-2999 | 128 | >64 | 0.25 |
| *Enterobacter cloacae* LSI-2943 | 16 | 32 | ≤0.06 |

[a]Determined at Laboratory Specialists, Inc. (Westlake, OH, USA) according to CLSI broth microdilution guidelines, all values in μg/mL.

[b]Very small pinpoint growth up to 4 μg/mL, no viable growth from pinpoint wells.

[c]Penicillin-susceptible.

[d]Penicillin-resistant.

[e]Vanconiycin-susceptible.

[f]Trailing observed; no viable growth within trailing wells.

[g]Vancomycin-resistant.

Evaluation of Gyease/TopoIV Dual-Inhibition in Biochemical and Whole Cell Assays The potent isomannide-derived NBTIs were evaluated for inhibition of both DNA gyrase and TopoIV from *S. aureus*, with the goal that balanced inhibition of both enzymes (dual targeting) would reduce the rate of resistance emergence (Strahilevitz, J., et at, Dual Targeting of Topoisomerase IV and Gyrase to Reduce Mutant Selection: Direct Testing of the Paradigm by Using WCK-1734, a New Fluoroquinolone, and Ciprofloxacin. *Antimicrob. Agents Chemother.* 2005, 49, 1949-1956; Nayar, A. S., et al., Target-Based Resistance in *Pseudomonas aeruginosa* and *Escherichia coil* to NBTI 5463, a Novel Bacterial Type II Topoisomerase Inhibitor. *Antimicrob. Agents Chemother.* 2015, 59, 331-337). As seen previously with other series of NBTIs (Mitton-Fry, M. J., et al., Novel Quinoline Derivatives as Inhibitors of Bacterial DNA Gyrase and Topoisomerase IV. *Bioorg. Med. Chem. Lett.* 2013, 23, 2955-2961), the isomannide-derived NBTIs inhibited *S. aureus* DNA gyrase more potently than TopoIV. Compounds 6, 24, and 26 did, however, show slightly more balanced ratios (~2-fold improvement) of TopoIV/gyrase $IC_{50}$ values as compared to dioxane 27.

TABLE 3

Inhibition of topoisomerase enzymes in biochemical assays

| Cmpd | Gyrase $IC_{50}$ (μM)[a] | TopoIV $IC_{50}$ (μM) | TopoIV/gyrase $IC_{50}$ ratio |
|---|---|---|---|
| 6 | 0.53 | 7.4 | 14 |
| 7 | 0.54 | No activity | Not determined |
| 24 | 0.2 | 2.6 | 13 |
| 25 | 0.18 | 7.5 | 42 |
| 26 | 0.2 | 2.9 | 15 |
| 27 | 0.03 | 1.0 | 33 |

[a]Determined at Inspiralis, Ltd. (Norwich, UK).

Determination of Spontaneous Frequencies of Resistance

In order to determine the spontaneous mutation frequency of investigational agents (Table 4), the MIC was first determined using the agar dilution method as recommended by the Clinical and Laboratory Standards Institute. This is because MIC values generated by agar vs. broth assays may differ, and the concentration of drug utilized in the spontaneous mutation assay must be as close to the agar dilution MIC as possible in order to produce meaningful results.

Serial dilutions of the test compounds (6 and 24) were made in DMSO; ciprofloxacin was diluted in water. Agar plates for selection of mutants were prepared by mixing 0.5 mL of concentrated drug (40× the agar dilution MIC) with 49.5 mL of molten (52° C.) Mueller-Hinton Agar (MHA), and pouring the mixture into 15-by-150 mm petri dishes. The plates were allowed to solidify and dry at room temperature prior to inoculation. Duplicate plates were prepared to contain the agents at 8× and 16× the median agar dilution MIC. In addition, duplicate 10×100 mm plates (standard small petri plates) were also prepared with 8× and 16× drug and were spot-inoculated with the standard inoculum density used for agar dilution according to CLSI; this was to confirm that the drug content of the plates was inhibitory for a standard inoculum thus validating that the stock drug content of the plates exceeded the MIC.

The inoculum for the assay was prepared by streaking *S. aureus* ATCC 29213 onto Mannitol Salt Agar (MSA; Hardy Diagnostics, Santa Maria, CA, No. 06231; Lot No. 422932) and incubating at 35° C. overnight. Using a single isolated colonies from the MSA plate, *S. aureus* was sub-cultured onto 10 TSAB plates and grown for approximately 20 hr at 35° C. Using a sterile swab, several well-isolated colonies were removed and resuspended in CAMHB at a heavy concentration equivalent to 1.7 on the turbidimeter to reach a target inoculum of $10^9$ to $10^{10}$ CFU on each spontaneous mutation plate. Each plate was inoculated with 0.25 mL of the cell suspension; each test concentration was inoculated onto two plates (except 6 which was inoculated onto a single plate for each test concentration due to insufficient drug volume) so that each drug was tested at 8× and 16× the MIC in duplicate. In addition, a portion of the inoculum was enumerated by making serial 10-fold dilutions, tracking them across the surface of a MHA plate, and counting colonies after a 24 hr incubation at 35° C.

Once the inoculum was absorbed into the agar, the drug-containing plates were incubated at 35° C. for 48 hr and the colonies resulting colonies were counted. The spontaneous mutation frequency was determined by dividing the number of colonies that appeared at a given drug concentration, averaging the counts from the duplicate plates, and dividing by the number of bacteria applied to the agar surface. Number of colonies were adjusted based on expected morphology (e.g. alpha hemolysis on TSAB) and/or confirmatory ID by MALDI.

The test agents and ciprofloxacin were assayed using a drug concentration range of 0.008-16 μg/mL. Triplicate independent inocula of *S. aureus* ATCC 29213 were evaluated.

Compounds 6 and 24 were also evaluated for their ability to suppress the emergence of NBTI-resistant mutants in a spontaneous frequency of resistance (FoR) study. At concentrations of 8× and 16×MIC, 24 proved superior to 6 but was unable to suppress the emergence of resistance completely. In contrast, no resistant mutants were obtained either at 8× or 16×MIC concentrations using ciprofloxacin. Thus, as with other NNTIs, these isomannide-derived NBTIs have not yet achieved the goal of ultra-low frequencies of spontaneous resistance in *S. aureus*. These results stand in contrast to those obtained using NBTI 5463 in *E. coil*, in which it was not possible to select resistant mutants using standard methodologies as a consequence of balanced inhibition of DNA gyrase and TopoIV in that organism.

TABLE 4

Spontaneous Frequency of Resistance.[a]

| Cmpd. | *S. aureus* ATCC 29213 MIC[b] (μg/mL) (n = 2) | Spontaneous mutation frequency (8X MIC) | Spontaneous mutation frequency (16X MIC) |
|---|---|---|---|
| 6 | 1 | $7.89 \times 10^{-8}$ (n = 1) | $1.57 \times 10^{-9}$ (n = 1) |
| 24 | 0.5 | $1.35 \times 10^{-9}$ (mean, n = 2) | $4.49 \times 10^{-10}$ (mean, n = 2) |
| ciprofloxacin | 0.5 | $<2.25 \times 10^{-10}$ | $<2.25 \times 10^{-10}$ |

[a]Determined at Micromyx, LLC (Kalamazoo, MI, USA).

[b]Assays were conducted according to CLSI agar dilution guidelines.

In Vitro Cardiovascular Safety Evaluation

The design of these isomannide-detived NBTIs focused on enhanced polarity and modulation of basicity through the two electronegative oxygen atoms in the linker. It was hypothesized that this alteration of physicochemical properties would correlate with reduced hERG inhibition, as observed previously. Consequently, hERG $IC_{50}$ values for compounds 6-7 and 24-26 were determined at Charles River (Cleveland, OH, USA) under the previously reported conditions (Table 5). Of these analogues, pyridodioxine 6 had the most favorable $IC_{50}$ (66 μM), being ca. 3-fold higher than benzodioxine 24 (20 μM). This shift is similar to observations with dioxane-linked NBTIs. Compounds 25 and 26, with monocyclic enzyme-binding motifs, showed greater hERG inhibition. It was expected that the pyridooxazinone 7 inhibit hERG quite potently on the basis of early observations in the dioxane series, but the $IC_{50}$ (12 μM) fell between the two other sets of compounds.

Evaluation of the safety hypothesis requires comparison to suitable analogues with different linkers. Table 5 also shows hERG $IC_{50}$ values, where available, for matched pairs of dioxane-linked and isomannide-derived analogues. Compounds 6, 7, and 24 are all superior to the corresponding dioxanes (28, 29, and 27, 2.5- to 8.5-fold), perhaps reflecting the lower lipophilicity (~0.7 cLogP units) and basicity (~0.6 pKa units) of the newer compounds. In contrast, highly lipophilic 26 was similar to the corresponding dioxane 30. A small set of compounds with a hydroxylated cyclohexane linker (WO 2004/035569 A2; Shapiro, A. B., et al., Allosteric Inhibition of the DNA-Dependent ATPase Activity of *Escherichia coil* DNA Gyrase by a Representative of a Novel Class of Inhibitors. *Biochem. Phainacot* 2012, 84, 900-904) (31-33) was also assayed. Such analogues are more basic (~1.8 pKa units) and more lipophilic (~0.7 cLogP units) than the isomannide-derived NBTIs. 31 and 32 are diastereomers of one another. The relative stereochemistry was not firmly proven, rather tentatively assigned based on a roughly 16-fold greater potency for 31 compared to 32 in the *S. aureus pk ATCC* 29213 MIC assay (0.063 vs. 1 μg/mL). Notably, 31 and 32 had identical hERG $IC_{50}$ values, and the analogous isomannide 24 was superior to both (>8-fold higher $IC_{50}$), further exemplifying the value of this new linker. This advantage was eroded, however, when comparing the 3,4-dichlorophenyl analogue 26 to 33. The stereochemistry of 33 was assigned based on greater similarity of its $^{1}H$ and $^{13}C$ NMR spectra to 32 compared to 31. Intriguingly, 33 still displayed a potent *S. aureus* ATCC 29213 MIC (0.125 μg/mL).

TABLE 5 hERG $IC_{50}$ values for isomannide-derived NBTIs and representative comparator compounds.

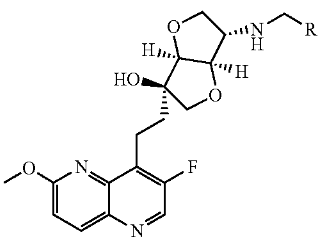

6-7, 24-26

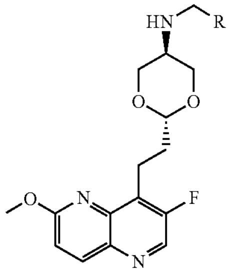

27-30

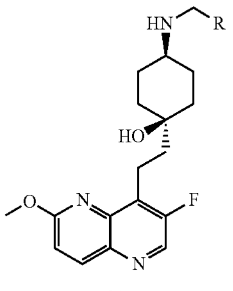

31

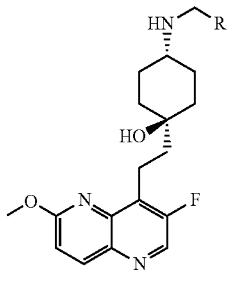

32-33

TABLE 5-continued

R =

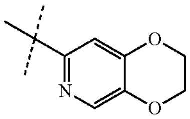

(6, 28)

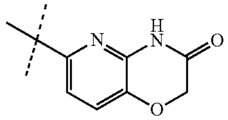

(7, 29)

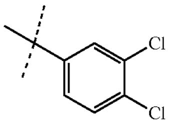

(26, 30, 33)

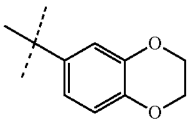

(24, 27, 31-32)

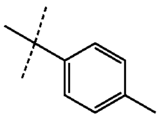

(25)

| Compound | Linker | RHS | hERG $IC_{50}$ (μM)[a] | cLogP[b] | pKa[b] |
|---|---|---|---|---|---|
| 6 | Novel | pyridodioxine | 66 | 2.5 | 6.9 |
| 7 | Novel | pyridooxazinone | 12 | 1.7 | 6.8 |
| 24 | Novel | benzodioxine | 20 | 3.2 | 7.5 |
| 25 | Novel | 4-methylphenyl | 4.2 | 3.8 | 7.6 |
| 26 | Novel | 3,4-di-Cl phenyl | 6.1 | 4.6 | 7.3 |
| 27 | Dioxane | benzodioxine | 8.0 | 3.9 | 8.1 |
| 28 | Dioxane | pyridodioxine | 15 | 3.2 | 7.4 |
| 29 | Dioxane | pyridooxazinone | 1.4 | 2.4 | 7.4 |
| 30 | Dioxane | 3,4-di-Cl phenyl | 7.9 | 5.3 | 7.9 |
| 31 | cyclohexane | benzodioxine | 2.2 | 3.9 | 9.3 |
| 32 | cyclohexane | benzodioxine | 2.3 | 3.9 | 3.9 |
| 33 | cyclohexane | 3,4-di-Cl phenyl | 3.8 | 5.3 | 9.1 |

[a]Determined using IonWorks Barracuda at Charles River (Cleveland, OH, USA) using previously reported methodology.
[b]Calculations carried out using Chemdraw Professional version 17.1.

Early drug discovery programs commonly assess hERG inhibition as the only indicator of potential cardiovascular safety concerns. Researchers have recently recommended a more rigorous evaluation of multiple cardiac ion channels to provide a more comprehensive cardiovascular risk assessment (Fermini, B., et al., A New Perspective in the Field of Cardiac Safety Testing through the Comprehensive In Vitro Proarrhythmia Assay Paradigm. *J. Biomolec. Screening* 2016, 21, 1-11). Given the promising initial results for 6, further evaluation was undertaken (in duplicate) in a Comprehensive in vitro Proarrhythmia Assay (CiPA) eight assay panel run on the QPatch HT (Sophion, Denmark) automated patch clamp system at three concentrations (3, 30, and 100 μM). All data were filtered for seal quality, seal drop, and current amplitude. A stock solution of the test compound at 30 mM concentration was prepared in DMSO.

Nav 1.5 Human Sodium Ion Channel Cell Based QPatch CiPA Assay

The parameters measured were the maximum inward current evoked on stepping to −15 mV from the test pulse. The peak current amplitude was calculated before and after compound addition and the amount of block was assessed by dividing the Test compound current amplitude by the Control current amplitude. Control is the mean hNav1.5 current amplitude collected 15 seconds at the end of the control; Test Compound is the mean hNav1.5 current amplitude collected in the presence of test compound at each concentration. The positive control compound was tetracaine.

hERG Human Potassium Ion Channel Cell Based QPatch CiPA Assay

The parameters measured were the maximum tail current evoked on stepping to 40 mV and ramping back to −80 mV from the test pulse. The peak current amplitude was calculated before and after compound addition and the amount of block was assessed by dividing the Test compound current amplitude by the Control current amplitude. Control is the mean hERG current amplitude collected 15 seconds at the end of the control; Test Compound is the mean hERG current amplitude collected in the presence of test compound at each concentration. The positive control was E-4031.

KCNQI/hminK Human Potassium Ion Channel Cell Based QPatch CiPA Assay

The parameters measured were the maximum outward current evoked on stepping to 60 mV from the test pulse. The peak current amplitude was calculated before and after compound addition and the amount of block was assessed by dividing the Test compound current amplitude by the Control current amplitude. Control is the mean hKCNQ1/hminK current amplitude collected 15 seconds at the end of the control; Test Compound is the mean hKCNQ1/hminK current amplitude collected in the presence of test compound at each concentration. The positive control was chromanol 293B.

Kir2.1 Human Potassium Ion Channel Cell Based QPatch CiPA Assay

The parameters measured were the maximum inward current evoked on stepping to −120 mV from the test pulse. The peak current amplitude was calculated before and after compound addition and the amount of block was assessed by dividing the Test compound current amplitude by the Control current amplitude. Control is the mean hKir2.1 current amplitude collected 15 seconds at the end of the control; Test Compound is the mean hKir2.1 current amplitude peak and end collected in the presence of test compound at each concentration. The positive control was barium chloride.

Kv4.3/KCIP2 Human Potassium Ion Channel Cell Based QPatch CiPA Assay

The parameters measured were the maximum outward current evoked on stepping to 40 mV from the test pulse. The peak current amplitude was calculated before and after compound addition and the amount of block was assessed by dividing the Test compound current amplitude by the Control current amplitude. Control is the mean hKv4.3/KChIP2 current amplitude collected 15 seconds at the end of the control; Test Compound is the mean hKv4.3/KChIP2 current amplitude peak and end collected in the presence of test compound at each concentration. The positive control was flecainide.

Cav1.2 (L-type; Human Calcium Ion Channel Cell Based QPatch CiPA Assay

The parameters measured were the maximum inward current evoked on stepping to 10 mV from the test pulse. The peak current amplitude was calculated before and after compound addition and the amount of block was assessed by dividing the Test compound current amplitude by the Control current amplitude. Control is the mean hCav1.2 current amplitude collected 15 seconds at the end of the control; Test Compound is the mean hCav1.2 current amplitude collected in the presence of test compound at each concentration. The positive control was nifedipine.

Nav1.5 Late Current Human Ion Channel Cell Based Agonist QPatch CiPA Assay

The parameters measured were the degree of activation of inward current (charge) evoked on stepping to −15 mV from the test pulse. The peak and ramp current (charge) amplitude was calculated before and after compound addition and the amount of current (charge) was assessed by dividing the Test compound current (charge) by the Control current (charge). Control is the mean hNav1.5 late current (charge) collected 15 seconds at the end of the control; Test Compound is the mean hNav1.5 current (charge) collected in the presence of test compound at each concentration. Changes in charge were normalized to the maximum response of the $EC_{50}$ of ATXII (positive control).

Nav1.5 Late Current Human Ion Channel Cell Based Antagonist QPatch CiPA Assay

The parameters measured were the maximum inward current (charge) evoked on stepping to −15 mV from the test pulse in the presence of 30 nM ATXII. The peak and ramp current (charge) amplitude was calculated before and after compound addition and the amount of current (charge) was assessed by dividing the Test compound current (charge) by the Control current (charge). Control is the mean hNav1.5 late current (charge) collected 15 seconds at the end of the control (30 nM ATXII); Test Compound is the mean hNav1.5 current (charge) collected in the presence of test compound and 30 nM ATXII at each concentration. The positive control was ranolizine.

The data (mean percent inhibition values) are shown in Table 6. Results demonstrate <50% inhibition at 100 μM for all of the six targets tested except for the Nav1.5 late current antagonist assay. This functional in vitro cardiovascular profile of the six cardiac targets predicts minimal preliminary proarrhythmic risk. An integrated assessment would be required to understand how the individual inhibitions for each target contribute to modifying the action potential shape. In addition, the results need to be compared to in vivo PK ($C_{max\ free}$) exposures to determine adequate safety margins.

Cytotoxicity in Mammalian Cells

The cytotoxicity of compound 6 was measured using an ATP viability assay in HepaRG cells, with a five-point concentration-response curve (Table 8). Even at the highest tested concentration (100 μM), only minimal cytotoxicity was observed (14%). Results indicate a substantial safety margin between the concentrations required to achieve anti-staphylococcal activity (MIC for *S. aureus* ATCC 29213=2-8 μM [1-4 μg/mL]) and the concentrations required to elicit toxicity in this cellular assay.

TABLE 8

Cytotoxicity of 6 in HepaRG cells.[a]

| Test Concentration (μM) | % Cytotoxicity |
|---|---|
| 100 | 14 |
| 10 | 8 |
| 1 | 9 |
| 0.1 | 4 |
| 0.01 | 6 |

[a]Conducted at RTI, International (Research Triangle Park, NC, USA).

ADME Assessment

Compound 6 was further evaluated in a series of ADME assays.

TABLE 6

Inhibition of cardiac ion channels by compound 6 at varying concentration.

| Ion Channel | % Inhibition at 3/30/100 μM |
|---|---|
| hERG (tail current) | −2.4/11.3/39.0 |
| KCNQ1 (peak current) | −2.9/1.5/22.1 |
| Kv4.3 (peak current) | 11.0/25.1/43.6 |
| Kv4.3 (end current) | −4.4/−19.6/7.1 |
| Kir2.1 (peak current) | 6.9/18/29.7 |
| Kir2.1 (end current) | 8.3/19.6/31.9 |
| Cav1.2 (peak current) | 4.7/23.3/24.9 |
| Nav1.5 (peak current) | 6.1/16.7/21.1 |
| Nav1.5 Late (antagonist - inhibition of ATXII $EC_{50}$ current) | 4.3/19.1/50.9 |
| Navi1.5 Late (agonist - activation of late current) | 3.4/7.7/17.0 |

[a]Conducted by Eurofins Panlabs (St. Charles, MO, USA).

Broader Safety Screening

Potential off-target pharmacology for compound 6 was also evaluated by screening in duplicate against a panel (Bowes, J., et al., Reducing Safety-Related Drug Attrition: The Use of in vitro Pharmacological Profiling. *Nat. Rev. Drug Disc.* 2012, 11, 909-922) of 44 receptors, enzymes, etc. Of the 44 potential targets, only five were inhibited by >50% at a concentration of 100 μM (Table 7).

TABLE 7

Targets inhibited by 6 by >50% at concentration of 100 μM.

| Assay | % Inhibition at 100 μM conc. |
|---|---|
| Histamine $H_2$ | 51 |
| Norepinephrine transporter | 68 |
| Nav site 2 | 78 |
| 5-$HT_{2B}$ | 95 |
| Dopamine transporter | 96 |

[a]Conducted by Eurofins Panlabs (St. Charles, MO, USA)

Aqueous Solubility—Kinetic Solubility

Test compounds were prepared at 10 mM in 100% DMSO and diluted into aqueous buffer, pH 7.4, to achieve a final test compound concentration of 100 μM with a final DMSO concentration of 1%. Caffeine and tamoxifen were assayed as control compounds. The samples were shaken for 90 minutes at room temperature and then filtered through a 0.4 μm filter plate. Filtrates were collected and analyzed using LC-MS/MS.

Plasma Protein Binding—Equilibrium Dialysis

In this assay an equilibrium dialysis technique was used to separate unbound test compound from compound bound to proteins. The plasma was spiked with the test compound at 10 μM with a final DMSO concentration of 1%. The dialysate compartment was loaded with phosphate buffered saline (PBS, pH 7.4) and the sample side was loaded with equal volume of the spiked plasma, After incubation at 37° C. for 4 hours, samples were removed from each plasma and buffer chamber; plasma protein was removed by treatment with acetonitrile. Recovered samples were analyzed using LC-MS.

Caco-2 Permeability

Caco-2 cells were plated on Transwell inserts and permeability assays were performed at day 21-25 post-plating. A single concentration of test compound (10 μM final) was prepared in HSS-HEPES buffer (pH 7.4) with a final DMSO concentration of 0.1%. To determine apical to basolateral (A to B) transport, test compounds were applied to the apical compartment in the presence and absence of the P-gp inhibitor verapamil (100 μM final). Atenolol and caffeine were assayed as control compounds. Samples were collected at various time points and analyzed using LC-MS/MS methods to determine the apparent permeability coefficient (Papp), efflux ratio, and recovery of the test compound.

Transport in the opposite direction (B to A) was also determined.

Cytotoxicity Assay—ATP Viability Assay

HepaRG cells were plated in a collagen coated 96-well plate overnight and treated the next day with test compounds and controls for 24 hours. Tamoxifen was used as a positive control compound for cytotoxicity (25 μM). After 24 hours, the plate was equilibrated to room temperature for 30 minutes and Cell Titer-Glo Reagent was added. Luminescence was measured using an EnSpire multimode plate reader. Data were reported as % cytotoxi city compared to vehicle treated control.

Cytotoxicity was determined by calculating the percentage of vehicle control:

$$\left(100 - \left(\left(\frac{\text{blank subtracted test compound } RLU}{\text{blank subtracted vehicle } RLU}\right) \times 100\right)\right) = \%\ \text{Cytotoxicity}$$

Microsomal Metabolic Stability

The test compound at 1 μM was pre-incubated with pooled liver microsomes in phosphate buffer (pH 7.4) for 5 minutes in a 37° C. shaking water bath. The reaction was initiated by adding NADPH-generating mixture (NADP+, glucose-6-phospate, glucose-6-phosphate dehydrogenase) and incubated for 0, 15, 30, 45, and 60 minutes. The reaction was stopped by transferring aliquots of the incubation mixture to acetonitrile/methanol. Samples were centrifuged, and supernatants analyzed by LCMS. The half-life was calculated from the slope of the initial linear range of the logarithmic curve of compound remaining %) vs. time, assuming first order kinetics. In addition, the intrinsic clearance (Clint) was calculated from the half-life.

Cytochrome P450 Inhibition in Human Liver Microsomes

CYP450 inhibition assays was conducted using individual enzyme substrates and inhibitors instead of a cocktail to avoid interferences. CYP450 isoforms tested included the following: CYP1A2, CYP2B6, CYP2C8, CYP2C9, CYP2C19, CYP2D6, and CYP3A4. Each test compound was screened at a final concentration of 10 μM. Each test compound was incubated with human liver microsomes (mixed gender, pool of 50 donors, 0.1 mg/mL), CYP450-selective probe substrates, and co-factors (NADPH, $MgCl_2$) in phosphate buffer (pH 7.4) for 10-30 min in a 96-well plate at 37° C. The reactions were stopped by transferring the reaction mixture to acetonitrile/methanol. Samples were mixed and centrifuged, and the supernatants analyzed by LC-MS/MS to quantify percent inhibition relative to vehicle control. If a test compound was active at 10 μM, then a follow up experiment was conducted with multiple compound concentrations (10 μM, 3 μM, 1 μM, 0.3 μM, and 0.1 μM) to determine the half maximal inhibitory concentration ($IC_{50}$) value.

Protein binding was moderately high in both mouse and human plasma, with unbound fractions of 4.7% and 13.8%, respectively. In buffered aqueous solution (pH 7.4), compound 6 was soluble at 76.2 μM. Permeability was high in Caco-2 cells (Yee, S. In Viiro Permeability Across Caco-2 Cells (Colonic) Can Predict In Vivo (Small Intestinal) Absorption in Man—Fact or Myth. *Pharmaceut. Res.* 1997, 14, 763-766) (A→B of $10.8\times10^{-6}$ cm/sec), and the compound showed higher permeability in the B→A direction ($85.3\times10^{-6}$ cm/sec), suggesting the potential for efflux. Using mouse and human microsomes, compound 6 demonstrated a very short half-life of 3 and 6 min, respectively, strongly suggesting the need for focused optimization of this key parameter, potentially by further reductions in lipophilicity (cLogP=2.5). Finally, inhibition of the cytochrome p450 enzymes was assessed at 10 μM. Less than 50% inhibition was seen for CYP1A2, 2B6, 2C9, 2C19, and 2D6. While 56% inhibition was observed for CYP3A4 in the screening assay at 10 μM concentration, a subsequent concentration-response assay in triplicate showed an $IC_{50}$>10 (Table 9). In summary, profiling of 6 as a representative of the isomannide-derived NBTI series revealed generally favorable drug-like properties, with the exception of rapid metabolism in microsomal assays.

TABLE 9

Concentration dependence of CYP3A4 (midazolam hydroxylase) by 6.

| Test Concentration (μM) | % of control (Exp. 1) | % of control (Exp. 2) | % of control (Exp. 3) |
|---|---|---|---|
| 10 | 49.5 | 82.3 | 74.5 |
| 3 | 74.3 | 77.2 | 60.4 |
| 1 | 60.4 | 89.8 | 89.9 |
| 0.3 | 89.9 | 113.1 | 99.2 |
| 0.1 | 115.5 | 108.4 | 97.0 |

[a]Conducted at RTI, International (Research Triangle Park, NC, USA).

MIC Determination Against *Mycobacterium tuberculosis* H37Rv and Clinically Relevant 1137Rv Derived Mono-Resistant Strains MICs were determined against Mtb H37Rv and 3 clinically relevant resistant strains using the microbroth dilution method. MIC was determined using optical density and a calorimetric growth indicator. For optical density ($OD_{600mm}$), the MIC is considered the first concentration to inhibit growth when compared to untreated growth control. For the calorimetric growth indicator (i.e.Alamar Blue), the MIC is calculated as the first concentration for the observed color change from pink, indicating active growth to blue, indicating no active growth.

MIC Determination against *Mycobacterium avium* and *Mycobacterium abscessus*

MICs were determined against the NTM strains 31 avium ATCC 700891 MAC101 and *M. abscessus* 19977 using the microbroth dilution method. MIC was determined using optical density and a calorimetric growth indicator. For optical density ($OD_{600mm}$), the MIC is considered the first concentration to inhibit growth when compared to an untreated growth control. A calorimetric growth indicator (i.e. Alamar Blue) was also added to confirm MIC value by observing color change from pink, indicating active growth to blue, indicating no active growth.

TABLE 10

| Minimum inhibitory concentrations (μg/mL) against *Mycobacterium tuberculosis*, *M. avium*, and *M. abscessus* | | | | | | |
|---|---|---|---|---|---|---|
| Compound | *M. tuberculosis* H37Rv | H37Rv (rpoB$^{S450L}$) | H37Rv (katG$^{del}$) | H37Rv (gyrA$^{D94K}$) | *M. abscessus* 19977 | *M. avium* 700891 |
| 25 | 8 | 4 | 4 | 16 | 8 | 16 |
| 26 | 2 | 1 | 1 | 2 | 8 | 1 |

Ex vivo Efficacy Against *M. tuberculosis*

To determine if compounds were cell permeable and had intracellular activity, intracellular activity of compounds against *M. tuberculosis H*37Rv was assessed in THP-1 macrophages. A standardized assay is to assess percent growth inhibition of *M. tuberculosis* during drug exposure under ex vivo conditions compared to in vitro determined MIC. This direct comparison method informs about cell permeability of the drug candidate and ability to inhibit growth of *M. tuberculosis* under growth conditions that approximates the in vivo environment.

*M. tuberculosis* infected THP-1 cells were treated in replicate at MIC concentrations as determined above. After exposure, the *M. tuberculosis* infected THP-1 cells were lysed, and growth inhibition measured compared to an untreated intracellular growth control. Compounds that are considered to have ex vivo activity against *M. tuberculosis* are able to inhibit >90+/−5% of the growth and had intermediate activity when inhibiting 50-85% of the growth compared to the untreated control. Positive controls isoniazid and rifampin were included and were within expected ranges with >90% inhibition at their respective MICs.

| Compound | *M. tuberculosis* ex vivo efficacy (% inhibition at MIC) |
|---|---|
| 25 | 80% |
| 26 | 90% |

Ex vivo Efficacy against *M. avium* and *M. abscessus* and cytotoxicity assays

Ex vivo efficacy was determined by inhibition of *Mycobacterium avium* complex (ATCC 700891 MAC 101), and *Mycobacterium abscessus* (ATCC 19977). Cytotoxicity tests were carried out against three human cell lines, THP-1 (ATCC TIB-202), HepG2 (ATCC HB-8065), and HeLa (ATCC CCL-2). $IC_{50}$ values were calculated from dose response curves to determine cytotoxicity of test compounds.

TABLE 11

| Ex vivo efficacy (μg/mL) against *M. avium* and *M. abscessus*, and cytotoxicity $IC_{50}$ values (μg/mL) | | | | | |
|---|---|---|---|---|---|
| Compound | *M. avium* (>90% inhibition) | *M. abscessus* (>90% inhibition) | THP-1 cytotoxicity | HepG2 cytotoxicity | HeLa cytotoxicity |
| 25 | >128 | >128 | 38.58 | 116.7 | 37.61 |
| 26 | >128 | 32 | 22.82 | 13.24 | 30.04 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

What is claimed is:

1. A compound having Formula I:

I

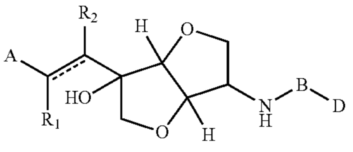

wherein the dashed line represents a bond that is present or absent, and when the bond is present, $R^1$ and $R^2$ can be cis or trans;

A has Formula II or III

II

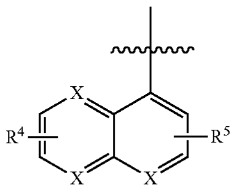

III

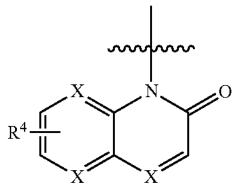

wherein each X is, independently, CH or N; or

A and $R^1$ together have Formula IX, X, XI, or XII

IX

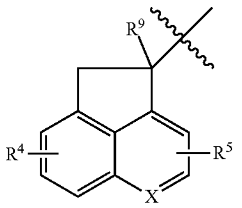

X

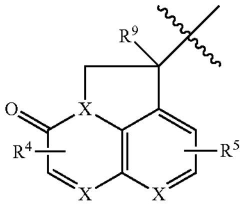

-continued

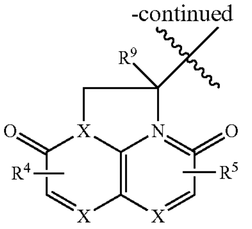

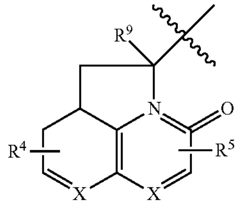

wherein each X is, independently, CH, N, or $CR^8$;

$R^4$ and $R^5$ are, independently, chosen from H, Cl, F, Br, I, CN, OH, $NO_2$, $NH_2$, $CF_3$, $CO_2H$, $CO_2NH_2$, $CO_2NHR_3$, $CO_2R^3$, $C(O)R^3$, $C(O)NH_2$, $C(O)NHR_3$, and $C_1$-$C_6$ alkyl or $C_1$-$C_6$ alkoxyl optionally substituted with $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

each $R^8$ is, independently, Cl, F, CN, OH, $OCH_3$, $CH_3$, or $NH_2$;

B is $C_1$-$C_6$ alkyl or $C_4$-$C_6$ cycloalkyl optionally substituted with one or more oxo, $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, nitro, silyl, sulfo-oxo, sulfonyl, sulfone, sulfoxide, or thiol;

D has Formula IV-VIII or XIII

IV

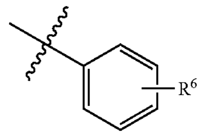

V

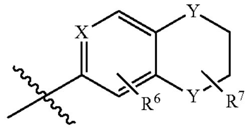

VI

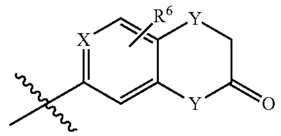

VII

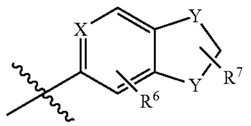

VIII

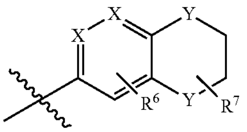

-continued

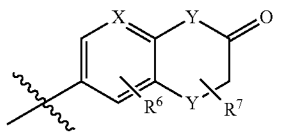

XIII wherein each X is, independently, chosen from CH or N;

each Y is, independently, chosen from O, S, NH, or $CH_2$;

$R^6$ and $R^7$ are, independently, chosen from H, Cl, F, Br, I, CN, OH, $NO_2$, $NH_2$, $CF_3$, $CO_2H$, $CO_2NH_2$, $CO_2NHR_3$, $CO_2R^3$, $C(O)R^3$, $C(O)NH_2$, $C(O)NHR_3$, and $C_1$-$C_6$ alkyl or $C_1$-$C_6$ alkoxyl optionally substituted with $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

$R^1$ and $R^2$ are, independently, chosen from H, OH, Cl, F, Br, I, CN, $NO_2$, $NH_2$, $CF_3$, $CO_2H$, $CO_2NH_2$, $CO_2NHR_3$, $CO_2R^3$, $C(O)R^3$, $C(O)NH_2$, $C(O)NHR_3$, oxo, and $C_1$-$C_6$ alkyl or $C_1$-$C_6$ alkoxyl optionally substituted with $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol, or $R^1$ is a $C_1$-$C_3$ alkyl or $C_2$-$C_3$ alkenyl, optionally substituted with $R^9$, also bound to A;

each $R^3$ is, independently, chosen from $C_1$-$C_6$ alkyl, $C_1$-$C_6$ cycloalkyl, $C_5$-$C_{15}$ aryl, $C_4$-$C_{15}$ heteroaryl, $C_3$-$C_{15}$ heterocycloalkyl, and $C_1$-$C_{15}$ heteroalkyl, any of which are optionally substituted with $C_1$-$C_6$ alkyl, $C_1$-$C_6$ alkoxyl, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, nitro, silyl, sulfo-oxo, sulfonyl, sulfone, sulfoxide, or thiol; and $R^9$ is H, Cl, F, Br, I, CN, OH, $NO_2$, $NH_2$, $CF_3$, $CO_2H$, $CO_2NH_2$, $CO_2NHR_3$, $CO_2R^3$, $C(O)R^3$, $C(O)NH_2$, $C(O)NHR_3$, or $C_1$-$C_6$ alkyl or $C_1$-$C_6$ alkoxyl optionally substituted with $C_1$-$C_{24}$ alkoxy, $C_2$-$C_{24}$ alkenyl, $C_2$-$C_{24}$ alkynyl, $C_5$-$C_{15}$ aryl, $C_4$-$C_{15}$ heteroaryl, aldehyde, amino, carboxylic acid, ester, ether, halide, hydroxy, ketone, cyano, nitro, silyl, sulfo-oxo, sulfonyl, sulfone, sulfoxide, or thiol;

or a pharmaceutically acceptable salt thereof.

2. The compound of claim 1, wherein $R^1$ and $R^2$ are, independently, chosen from H, F, CN, OH, and $NH_2$.

3. The compound of claim 1, wherein $R^2$ is $NH_2$.

4. The compound of claim 1, wherein $R^2$ is H or OH.

5. The compound of claim 1, wherein A has Formula II and $R^4$ and $R^5$ are, independently, chosen from H, Cl, F, Br, I, CN, OH, and unsubstituted $C_1$-$C_6$ alkyl or $C_1$-$C_6$ alkoxyl.

6. The compound of claim 1, wherein A has Formula II and $R^4$ and $R^5$ are, independently, chosen from H, Cl, F, OH, and methoxyl.

7. The compound of claim 1, wherein A has Formula II and $R^4$ and $R^5$ are, independently, chosen from F and methoxyl.

8. The compound of claim 1, wherein A has Formula II and two X's are N and the other X is CH.

9. The compound of claim 1, wherein A has Formula II and two X's are CH and the other X is N.

10. The compound of claim 1, wherein A has Formula III and $R^4$ is chosen from H, Cl, F, Br, I, OH, and unsubstituted $C_1$-$C_6$ alkyl or $C_1$-$C_6$ alkoxyl.

11. The compound of claim 1, wherein A has Formula III and $R^4$ is chosen from H, Cl, F, OH, and methoxyl.

12. The compound of claim 1, wherein A has Formula III and $R^4$ is chosen from F and methoxyl.

13. The compound of claim 1, wherein A and $R^1$ together have Formula IX, X, XI, or XIII and $R^4$ is H and $R^5$ is F.

14. The compound of claim 1, wherein B is unsubstituted methyl, ethyl, propyl, butyl, cyclobutyl, or cyclopentyl.

15. The compound of claim 1, wherein B is $CH_2$ or cyclobutyl.

16. The compound of claim 1, wherein $R^6$ and $R^7$ are, independently, chosen from H, Cl, F, Br, I, CN, OH, and unsubstituted $C_1$-$C_6$ alkyl or $C_1$-$C_6$ alkoxyl.

17. The compound of claim 1, wherein $R^6$ and $R^7$ are, independently, chosen from H, Cl, F, CN, OH, and methoxyl.

18. The compound of claim 1, wherein $R^6$ and $R^7$ are both H.

19. The compound of claim 1, wherein both Y are O.

20. The compound of claim 1, wherein one Y is S and the other is O.

21. The compound of claim 1, wherein one Y is NH and the other is O.

22. The compound of claim 1, wherein one Y is NH and the other is S.

23. The compound of claim 1, wherein the dashed line is a bond that is present.

24. The compound of claim 1, wherein the dashed line is a bond that absent.

25. A compound chosen from (3R,3aS,6S,6aR)-6-(((2,3-dihydro-[1,4]dioxino[2,3-c]pyridin-7-yl)methyl)amino)-3-(2-(3-fluoro-6-methoxy-1,5-naphthyridin-4-yl)ethyl)hexahydrofuro[3,2-b]furan-3-ol (compound 6);

6-((((3S,3aR,6R,6aS)-6-(2-(3-fluoro-6-methoxy-1,5-naphthyridin-4-yl)ethyl)-6-hydroxyhexahydrofuro[3,2-b]furan-3-yl)amino)methyl)-2H-pyrido[3,2-b][1,4]oxazin-3 (4H)-one (compound 7);

2-((3S,3aR,6R,6aS)-6-hydroxy-6-((E)-2-(6-methoxyquinolin-4-yl)vinyl)hexahydrofuro[3,2-b]furan-3-yl) isoindoline-1,3-dione (compound 15);

2-((3S,3aR,6R,6aS)-6-((E)-2-(3-fluoro-6-methoxy-1,5-naphthyridin-4-yl)vinyl)-6-hydroxyhexahydrofuro[3,2-b]furan-3-yl) isoindoline-1,3-dione (compound 16);

2-((3S,3aR,6R,6aS)-6-hydroxy-6-(2-(6-methoxyquinolin-4-yl)ethyl)hexahydrofuro[3,2-b]furan-3-yl) isoindoline-1,3-dione (compound 17);

2-((3S,3aR,6R,6aS)-6-(2-(3-fluoro-6-methoxy-1,5-naphthyridin-4-yl)ethyl)-6-hydroxyhexahydrofuro[3,2-b]furan-3-yl) isoindoline-1,3-dione (compound 18);

(3R,3aS,6S,6aR)-6-(((2,3-dihydrobenzo[b][1,4]dioxin-6-yl)methyl)amino)-3-(2-(6-methoxyquinolin-4-yl)ethyl)hexahydrofuro[3,2-b]furan-3-ol (compound 21);

(3R,3aS,6S,6aR)-6-(benzylamino)-3-(2-(6-methoxyquinolin-4-yl)ethyl)hexahydrofuro[3,2-b]furan-3-ol (compound 22);

(3R,3aS,6S,6aR)-3-(2-(6-methoxyquinolin-4-yl)ethyl)-6-((4-methylbenzyl)amino)hexahydrofuro[3,2-b]furan-3-ol (compound 23);

(3R,3aS,6S,6aR)-6-(((2,3-dihydrobenzo[b][1,4]dioxin-6-yl)methyl)amino)-3-(2-(3-fluoro-6-methoxy-1,5-naphthyridin-4-yl)ethyl)hexahydrofuro[3,2-b]furan-3-ol (compound 24);

(3R,3aS,6S,6aR)-3-(2-(3-fluoro-6-methoxy-1,5-naphthyridin-4-yl)ethyl)-6-((4-methylbenzyl)amino)hexahydrofuro[3,2-b]furan-3-ol (compound 25); or (3R,3aS,6S,6aR)-6-((3,4-dichlorobenzyl)amino)-3-(2-(3-fluoro-6-methoxy-1,5-naphthyridin-4-yl)ethyl)hexahydrofuro[3,2-b]furan-3-ol (compound 26).

26. The compound of claim 1, wherein the compound is a type II topoisomerase inhibitor.

27. A method of treating an infection in a subject, comprising administering to the subject an effective amount of the compound of claim 1.

28. The method of claim 27, wherein the infection is a *Staphylococcus aureus* infection.

29. The method of claim 27, wherein the infection is a methicillin-resistant *S. aureus* (MRSA) infection.

30. The method of claim 27, wherein the infection is an *M. tuberculosis* infection.

31. The method of claim 27, wherein the subject has cystic fibrosis.

32. The compound of claim 1, wherein $R^1$ is H or OH.

* * * * *